(12) United States Patent
Nam et al.

(10) Patent No.: US 8,081,825 B2
(45) Date of Patent: Dec. 20, 2011

(54) METHOD FOR REALTIME TARGET DETECTION BASED ON REDUCED COMPLEXITY HYPERSPECTRAL PROCESSING

(75) Inventors: Yun Young Nam, Suwon-si (KR); Sang Jin Hong, New York, NY (US); We Duck Cho, Seongnam-si (KR); Kyoung Su Park, Suwon-si (KR)

(73) Assignee: Ajou University Industry Cooperation Foundation, Gyeonggi-Do (KR)

( * ) Notice: Subject to any disclaimer, the term of this patent is extended or adjusted under 35 U.S.C. 154(b) by 0 days.

(21) Appl. No.: 12/918,300

(22) PCT Filed: Apr. 2, 2008

(86) PCT No.: PCT/KR2008/001840
§ 371 (c)(1),
(2), (4) Date: Aug. 18, 2010

(87) PCT Pub. No.: WO2009/107893
PCT Pub. Date: Sep. 3, 2009

(65) Prior Publication Data
US 2010/0329512 A1    Dec. 30, 2010

(30) Foreign Application Priority Data

Feb. 27, 2008   (KR) .................. 10-2008-0017674

(51) Int. Cl.
*G06K 9/46*     (2006.01)
(52) U.S. Cl. ....................................... 382/191; 356/303

(58) Field of Classification Search .................. 382/100, 382/103, 181, 190, 191, 224, 226, 303; 356/300, 356/303
See application file for complete search history.

(56) References Cited

U.S. PATENT DOCUMENTS

| | | | |
|---|---|---|---|
| 6,282,301 B1 * | 8/2001 | Haskett ........................ | 382/103 |
| 6,771,798 B1 * | 8/2004 | Haas et al. .................... | 382/103 |
| 6,813,380 B1 | 11/2004 | Sola et al. ..................... | 382/191 |
| 7,040,570 B2 * | 5/2006 | Sims et al. .................... | 244/3.16 |
| 7,194,111 B1 * | 3/2007 | Schaum et al. ............... | 382/103 |
| 7,450,761 B2 * | 11/2008 | Portigal et al. ................ | 382/191 |
| 7,956,761 B2 * | 6/2011 | Polak et al. ................... | 340/632 |
| 2006/0221335 A1 | 10/2006 | Pangalore et al. ............ | 356/301 |

OTHER PUBLICATIONS

Banerjee et al. (2006), "A Support Vector Method for Anomaly Detection in Hyperspectral Imagery", *IEEE Transactions on Geoscience and Remote Sensing*, 44(8):2282-2291.
International Search Report in PCT/KR2008/001840 published Nov. 13, 2008.
Schweizer et al. (2000), "Hyperspectral Imagery: Clutter Adaption in Anomaly Detection", *IEEE Transactions on Information Theory*, 46(5):1855-1871.
Schweizer et al. (2001), "Efficient Detection in Hyperspectral Imagery", *IEEE Transactions on Information Theory*, 10(4):584-597.

* cited by examiner

*Primary Examiner* — Anand Bhatnagar
(74) *Attorney, Agent, or Firm* — Harness, Dickey & Pierce, P.L.C.; Anthony G. Fussner; Kisuk Lee

(57) ABSTRACT

There is provided a method for real-time target detection comprising detecting a preprocessed pixel as a target and/or a background, based on a library, and refining the library by extracting a sample from the target or the background.

5 Claims, 22 Drawing Sheets

(a) $N_E = 4$ (b) $N_E = 31$

[FIG. 1]
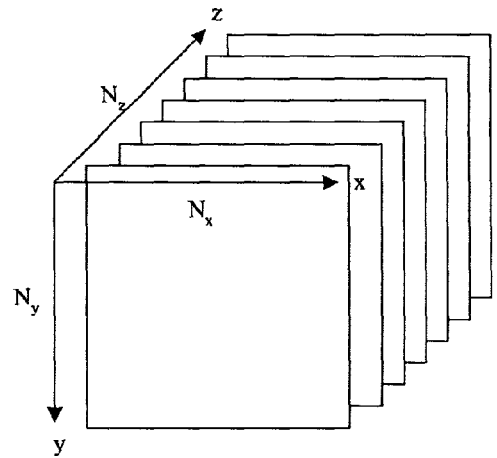
[FIG. 2]
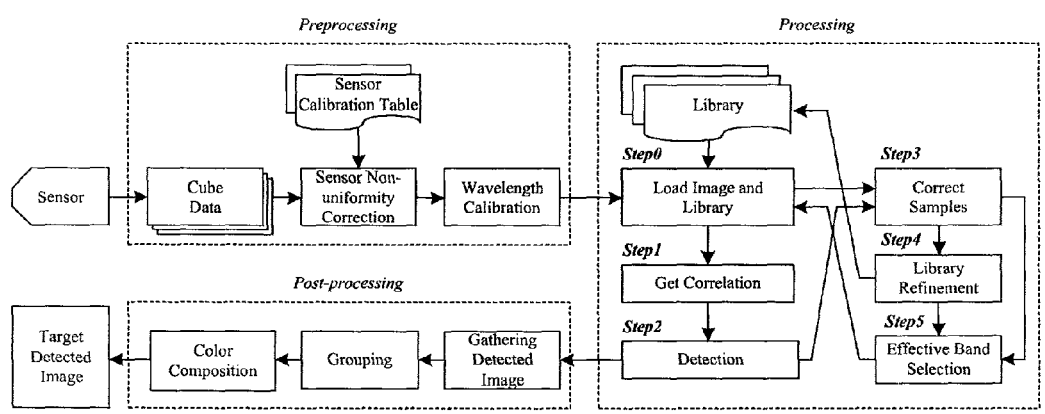

[FIG. 3]
 
(a) $N_E = 4$    (b) $N_E = 31$
[FIG. 4]
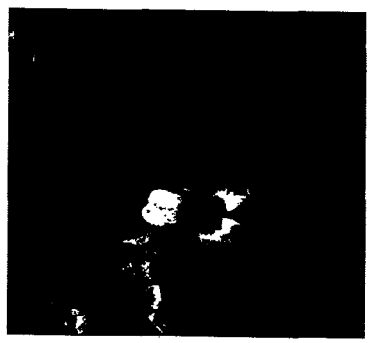  
(a) Initial detection    (b) Detection after first iteration    (c) Detection after second iteration

[FIG. 5]
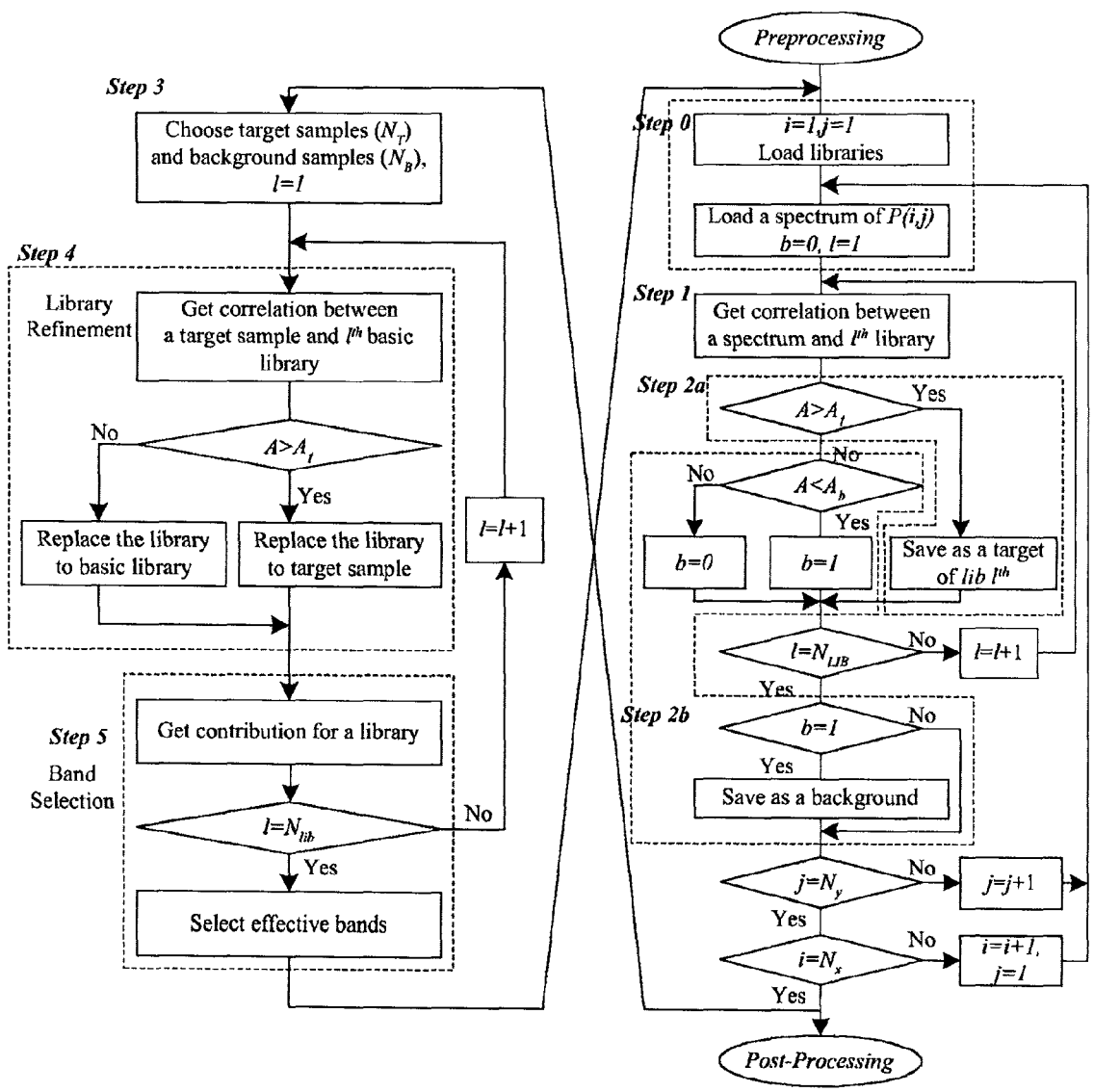

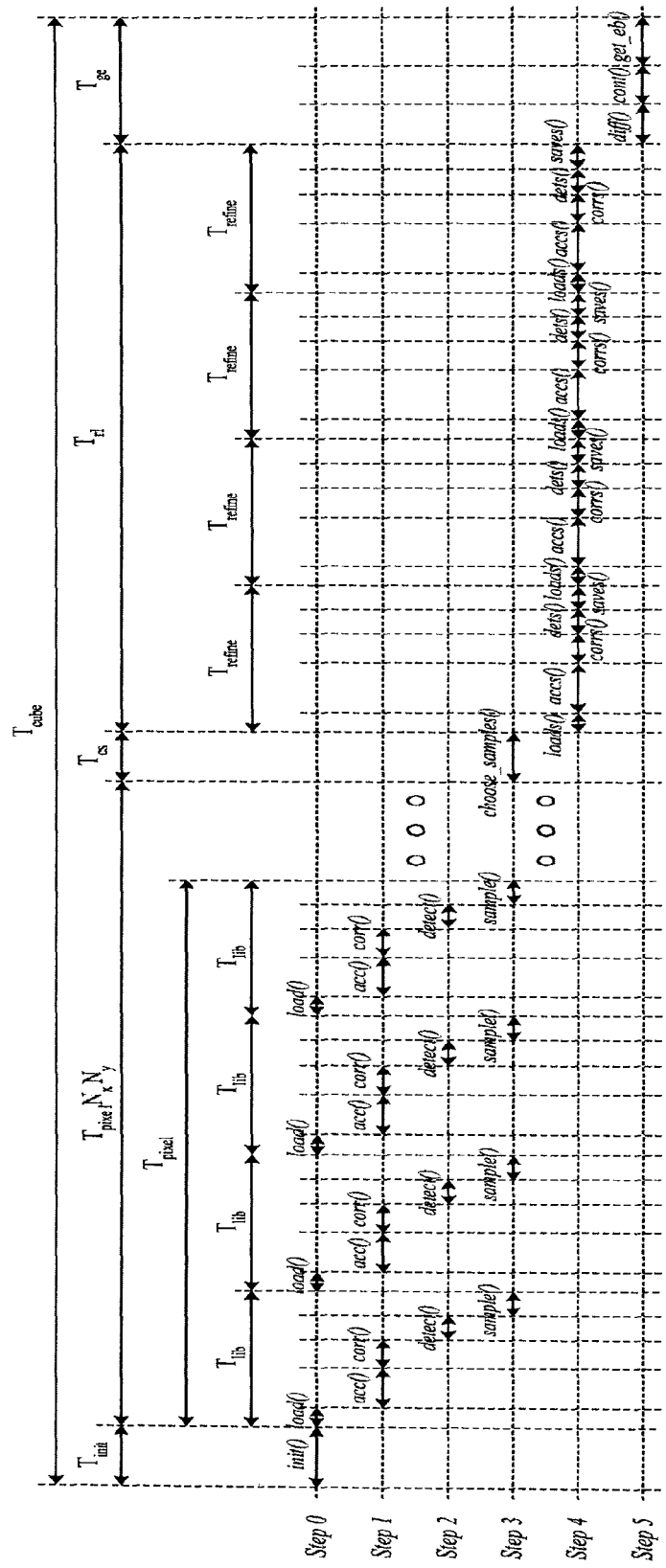
[FIG. 6]

[FIG. 7]
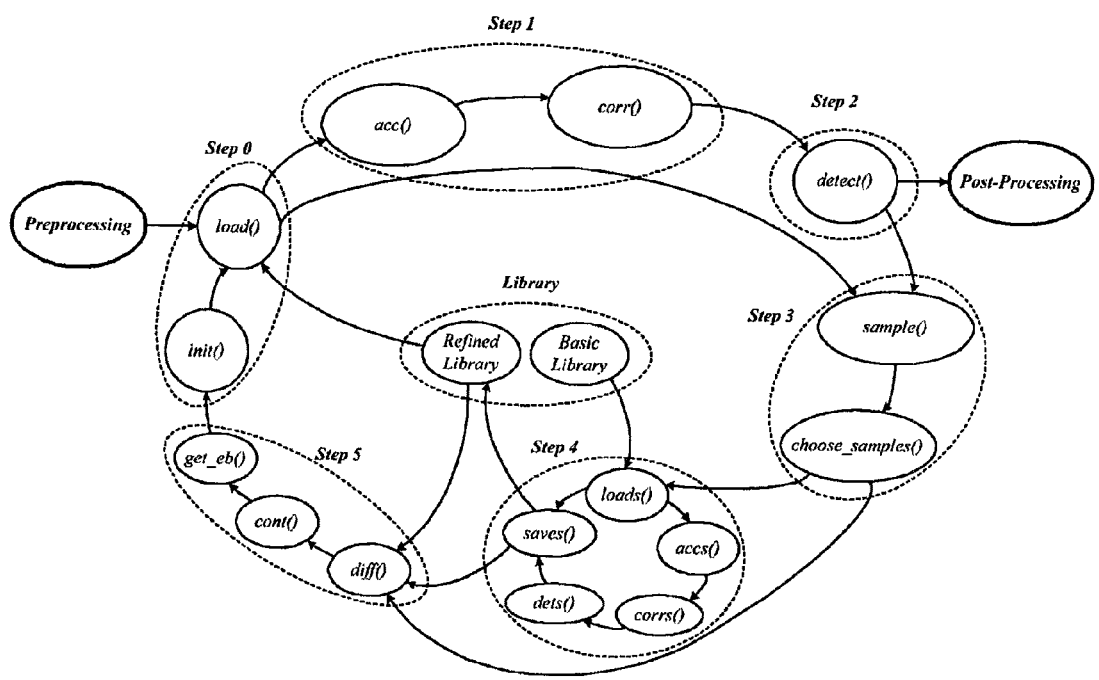

[FIG. 8]
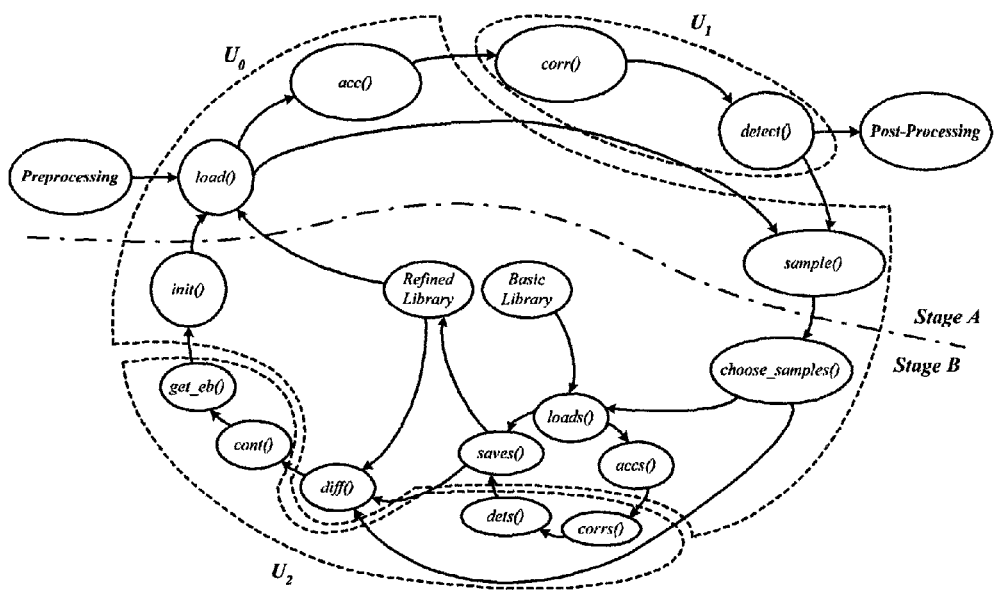
[FIG. 9]
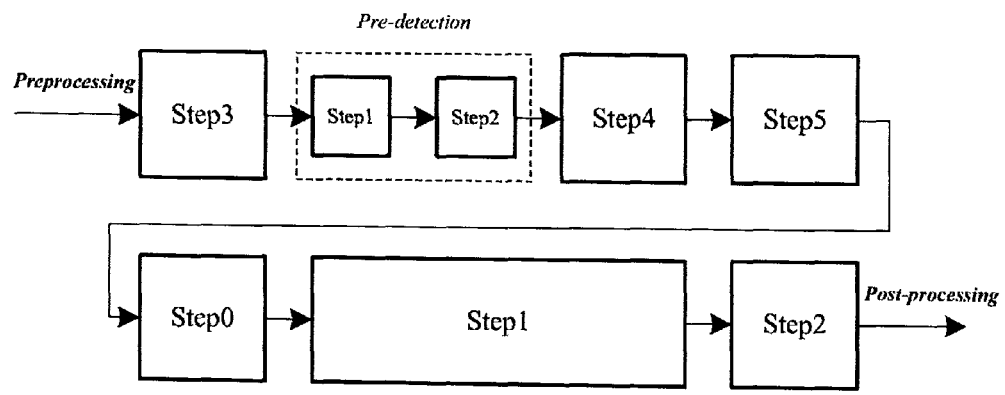

[FIG. 10]
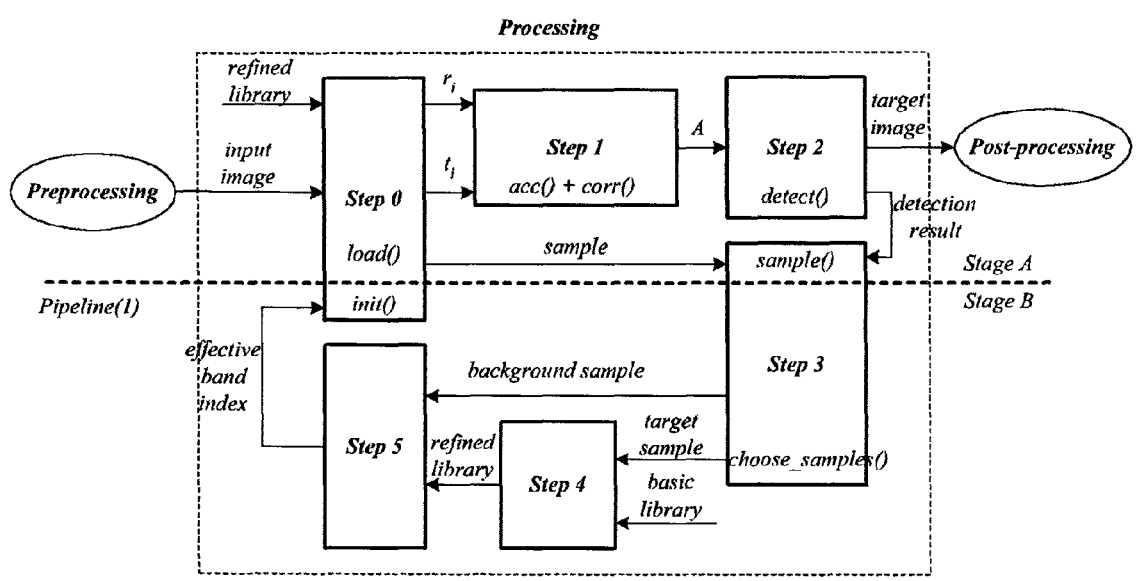

[FIG. 11]
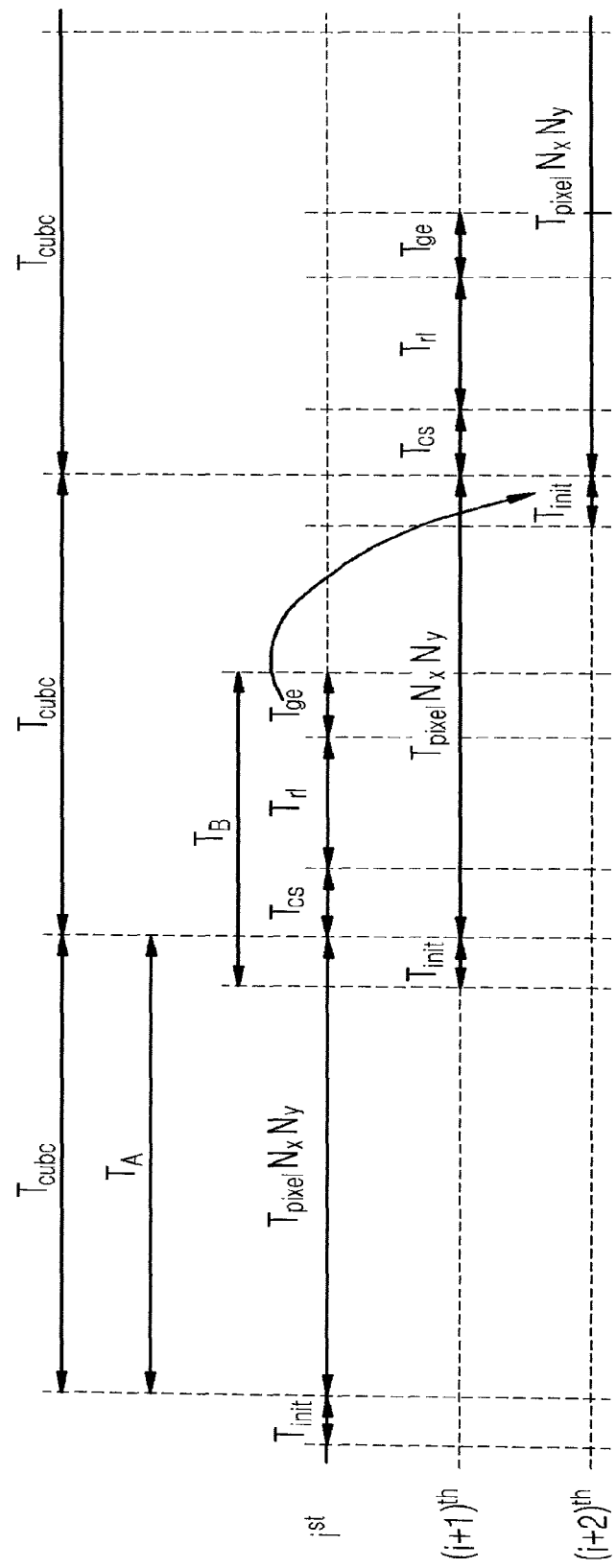

[FIG. 12]
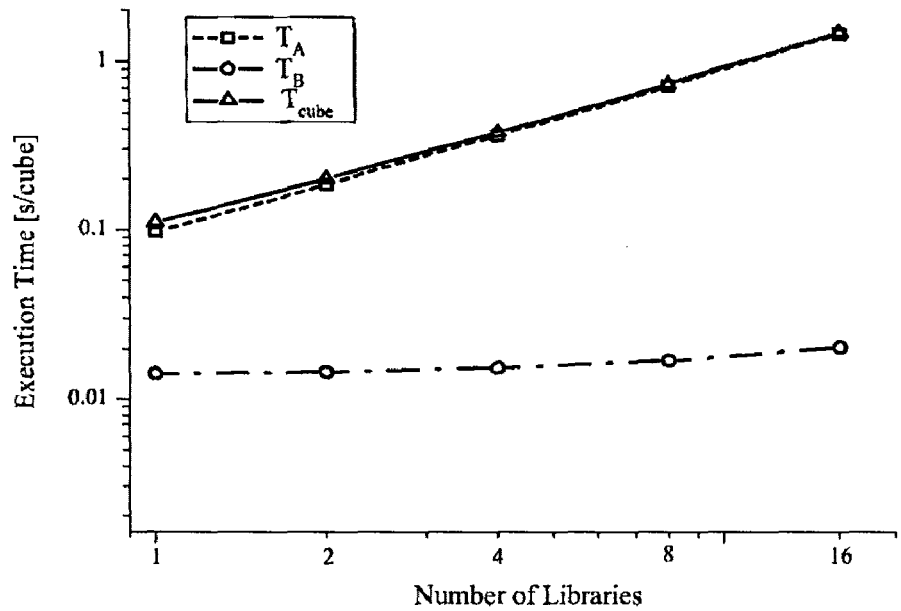
(a) for $N_{LIB}$ ($N_E = 4$)
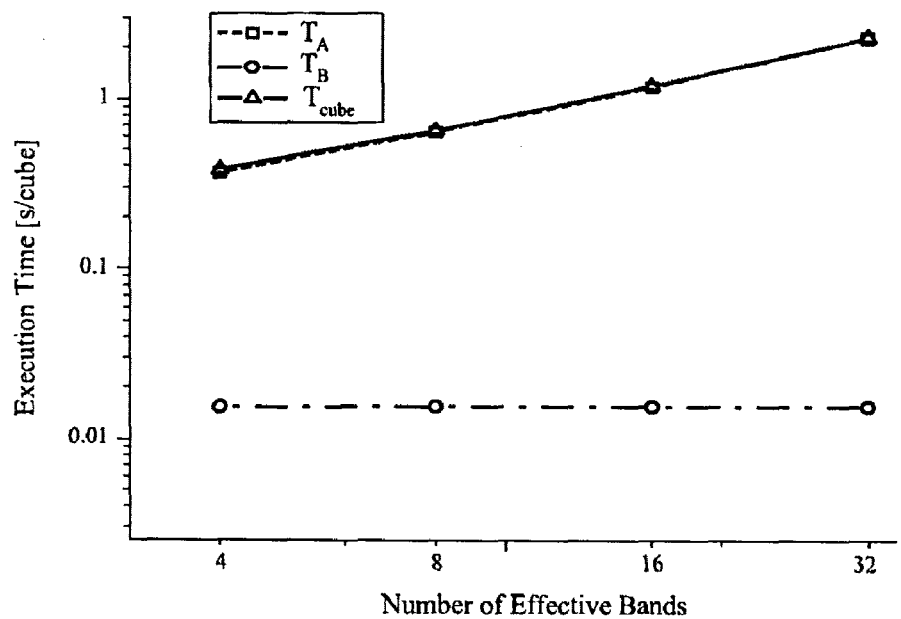
(b) for $N_E$ ($N_{LIB} = 4$)

[FIG. 13]
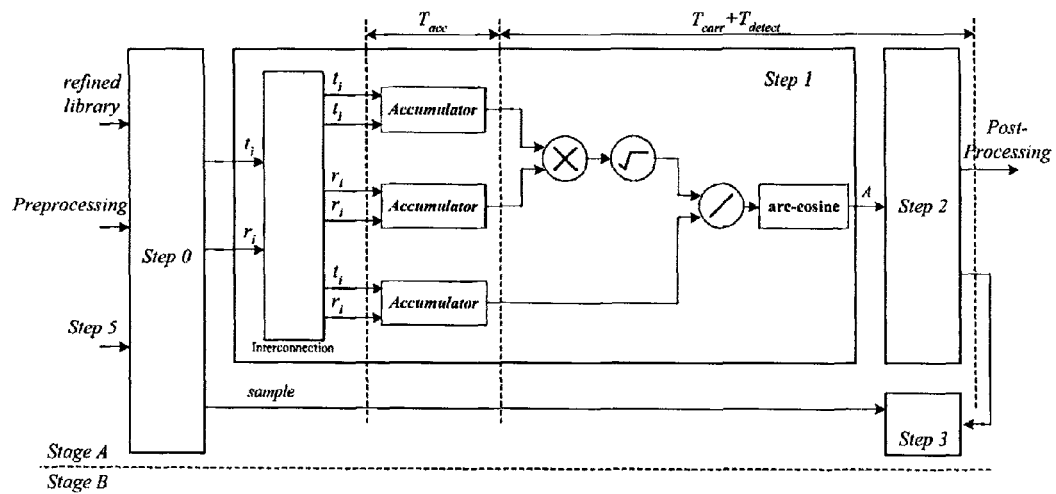
[FIG. 14]
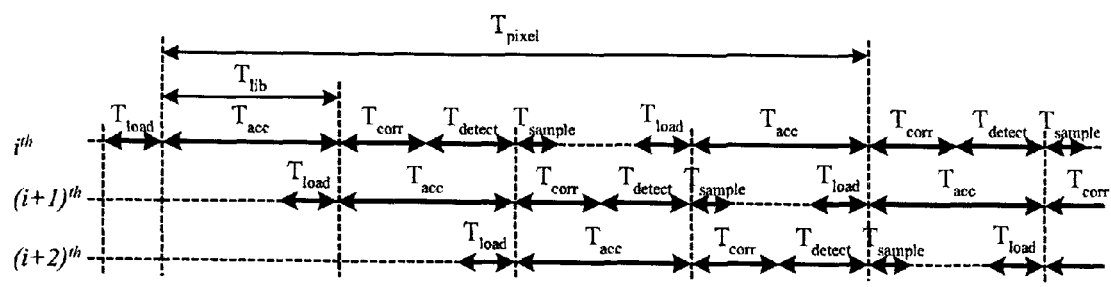

[FIG. 15]
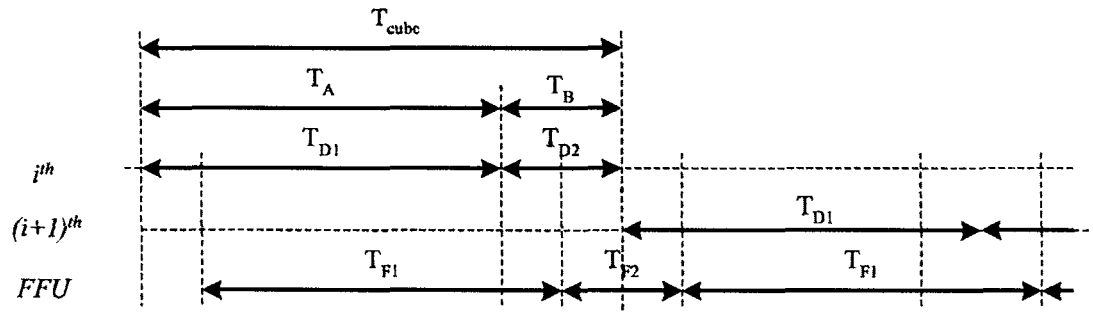
(a) With one floating point processor
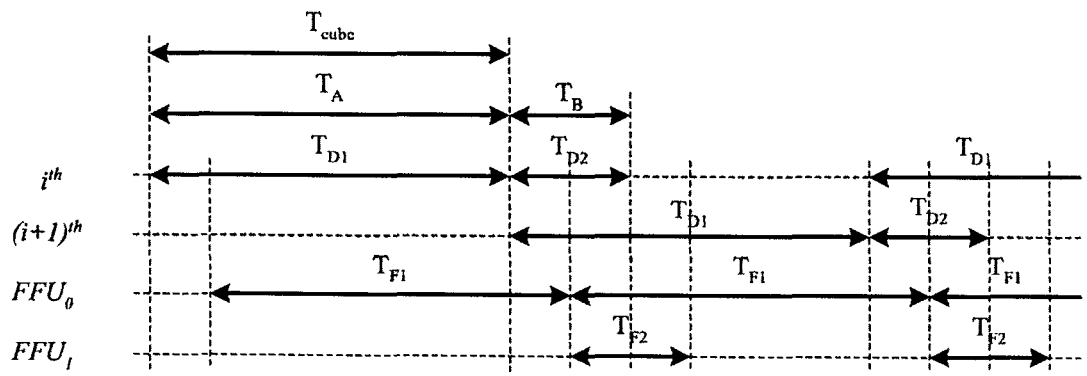
(b) With two floating point processors (case 1)
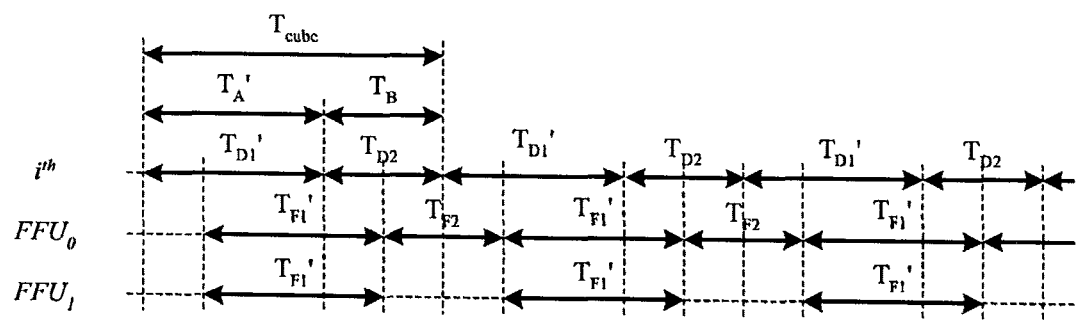
(c) With two floating point processors (case 2)

[FIG. 16]
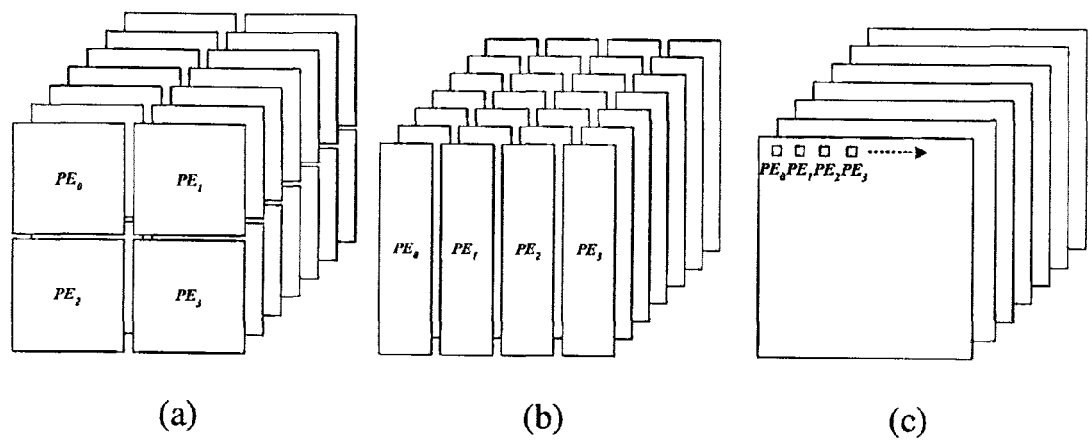
(a)  (b)  (c)
[FIG. 17]
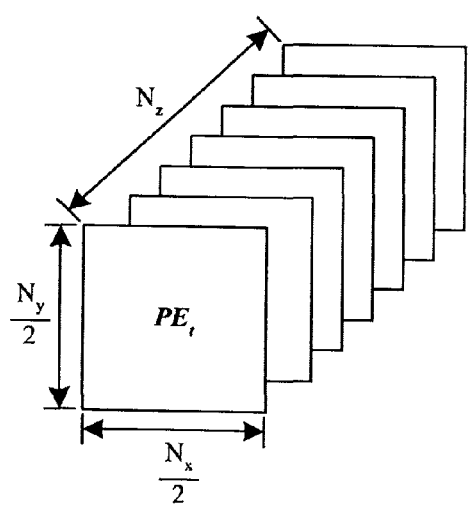

[FIG. 18]
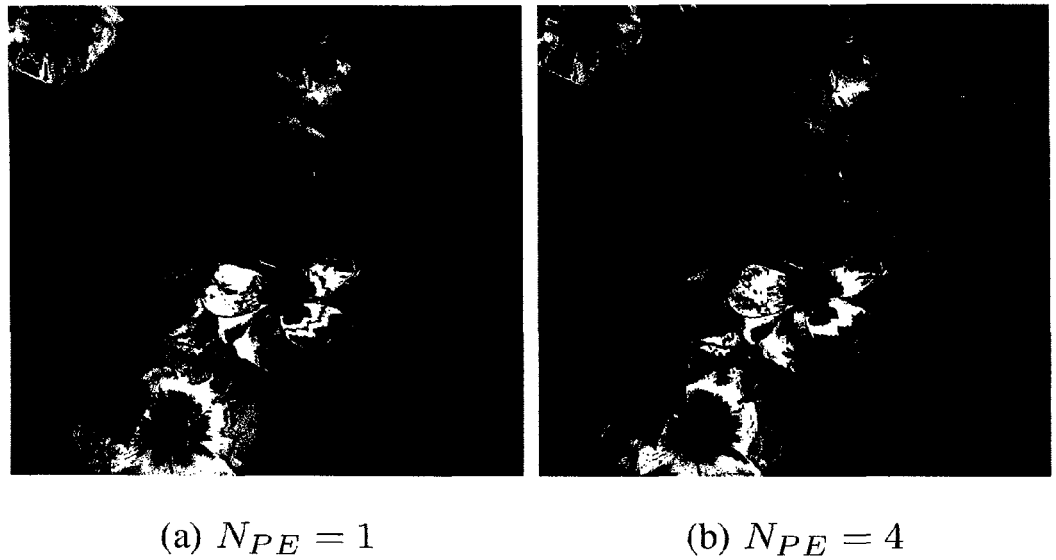
(a) $N_{PE} = 1$     (b) $N_{PE} = 4$
[FIG. 19]
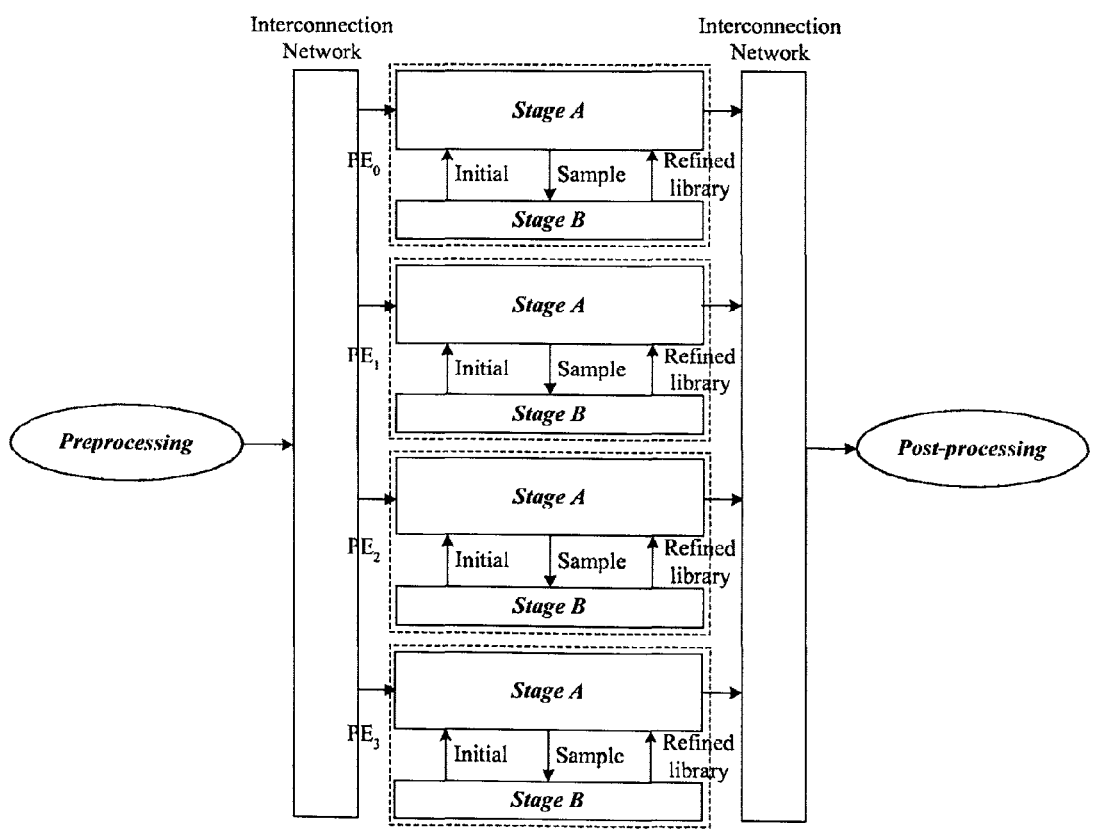

[FIG. 20]
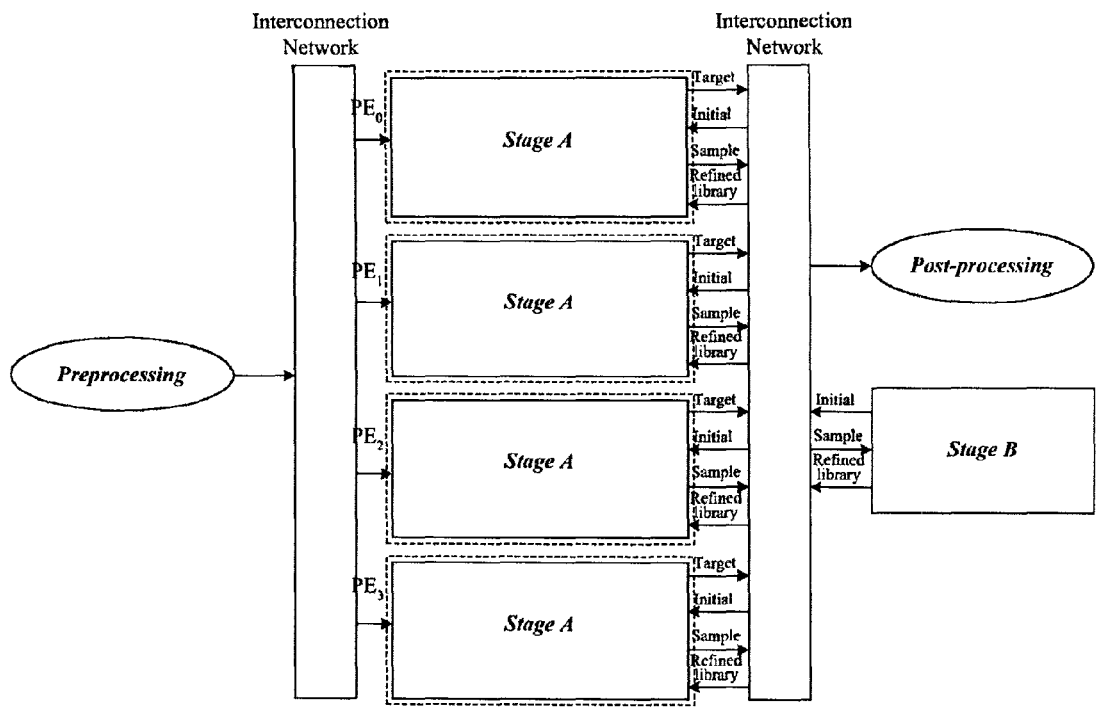
[FIG. 21]
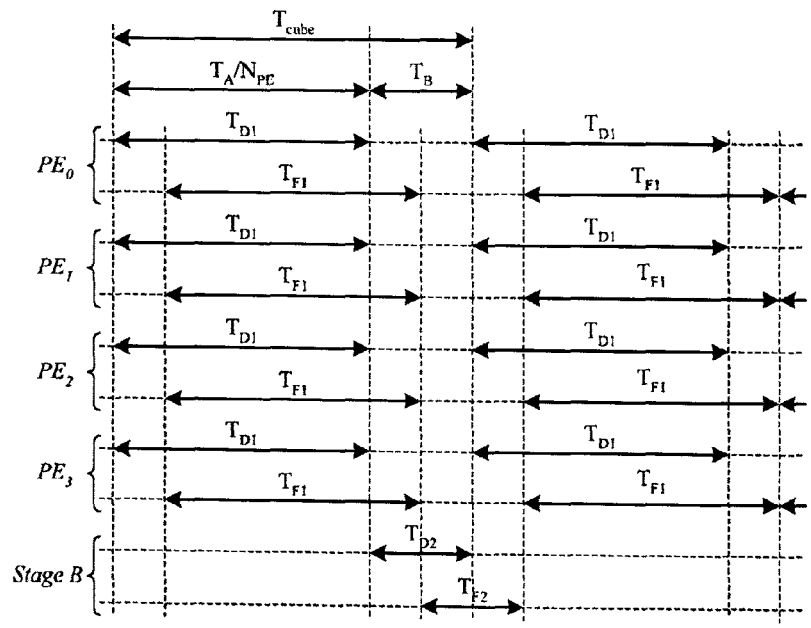

[FIG. 22]
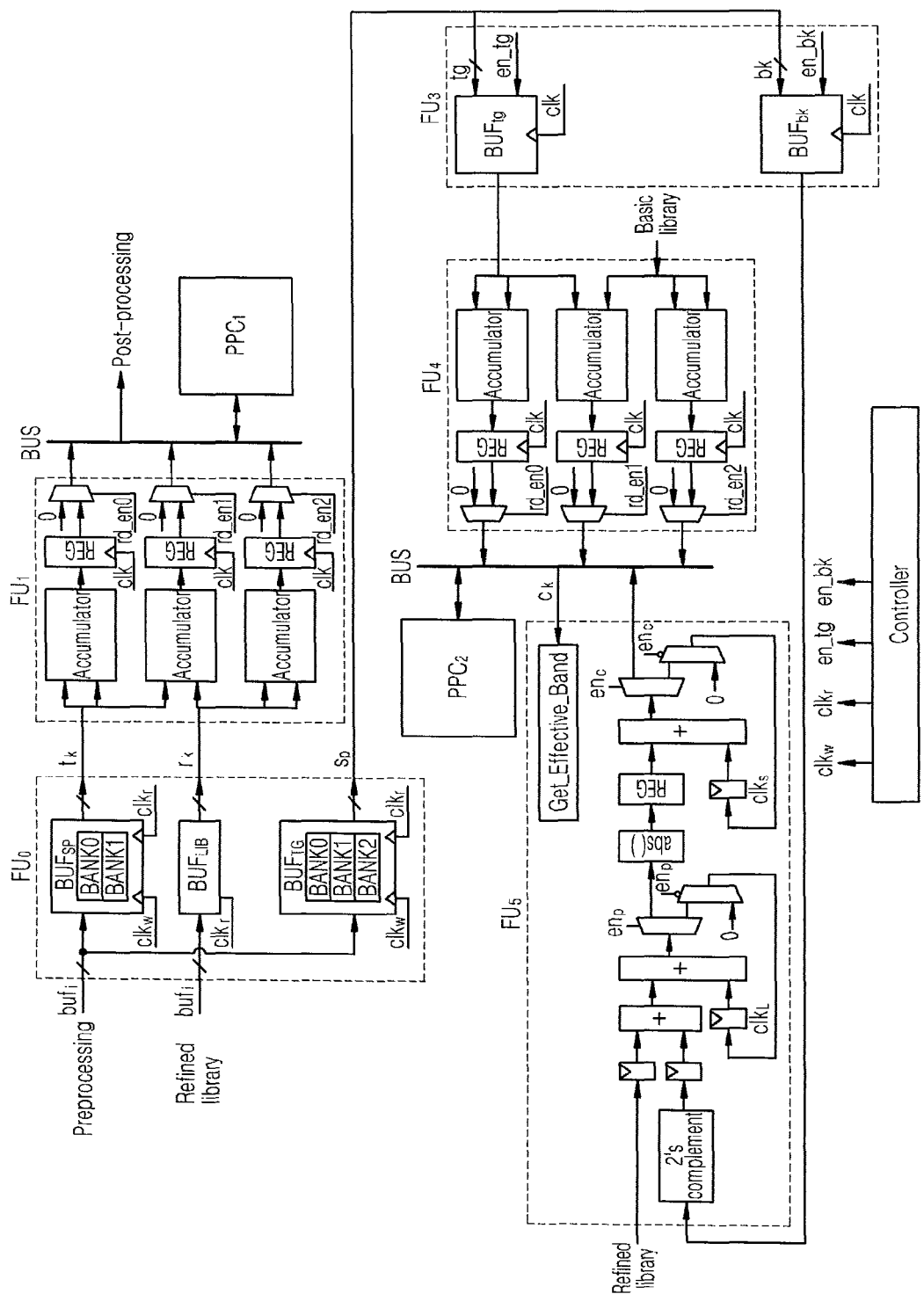

[FIG. 23]
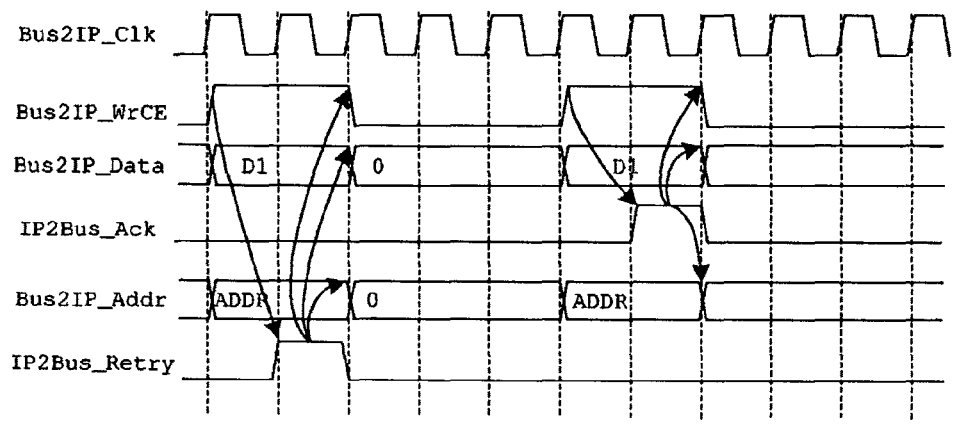
[FIG. 24]
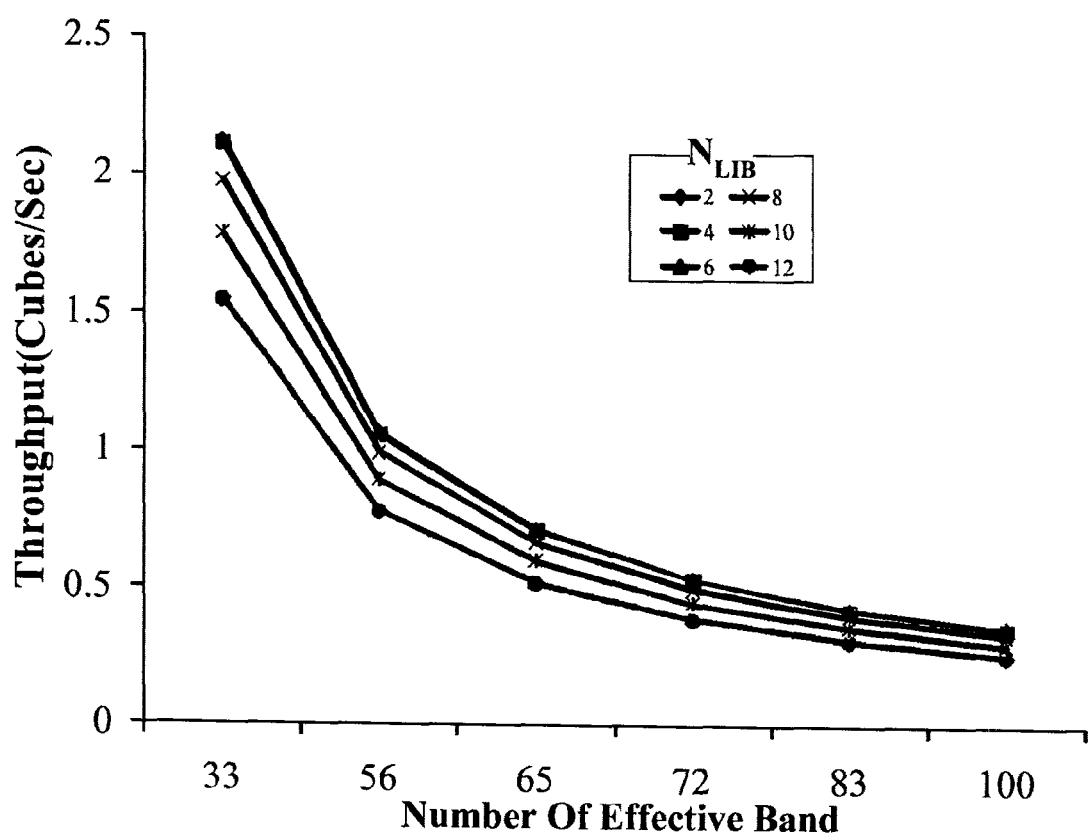

[FIG. 25]
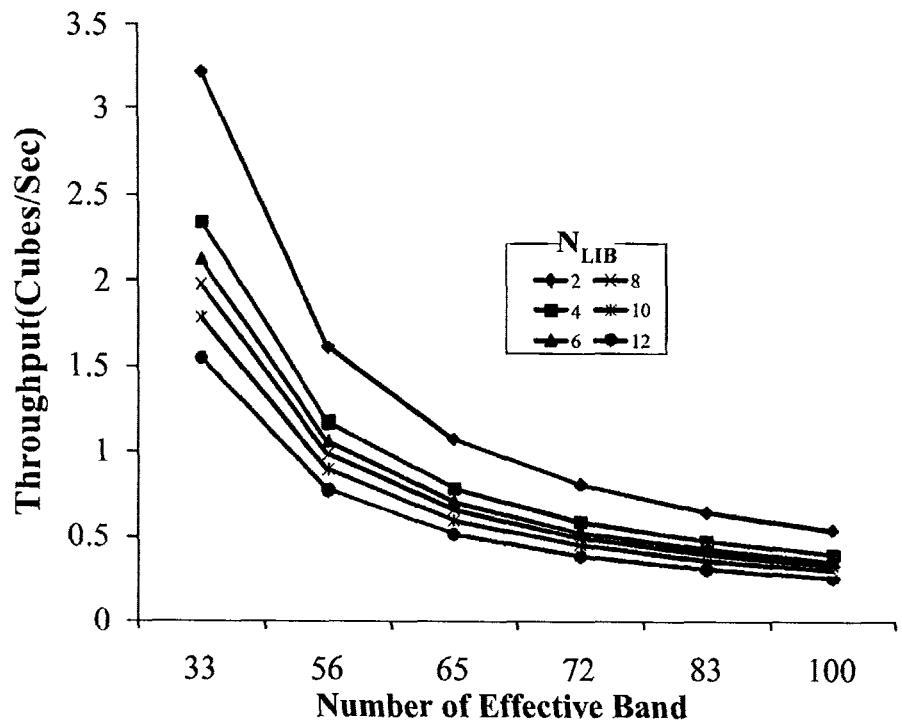
[FIG. 26]
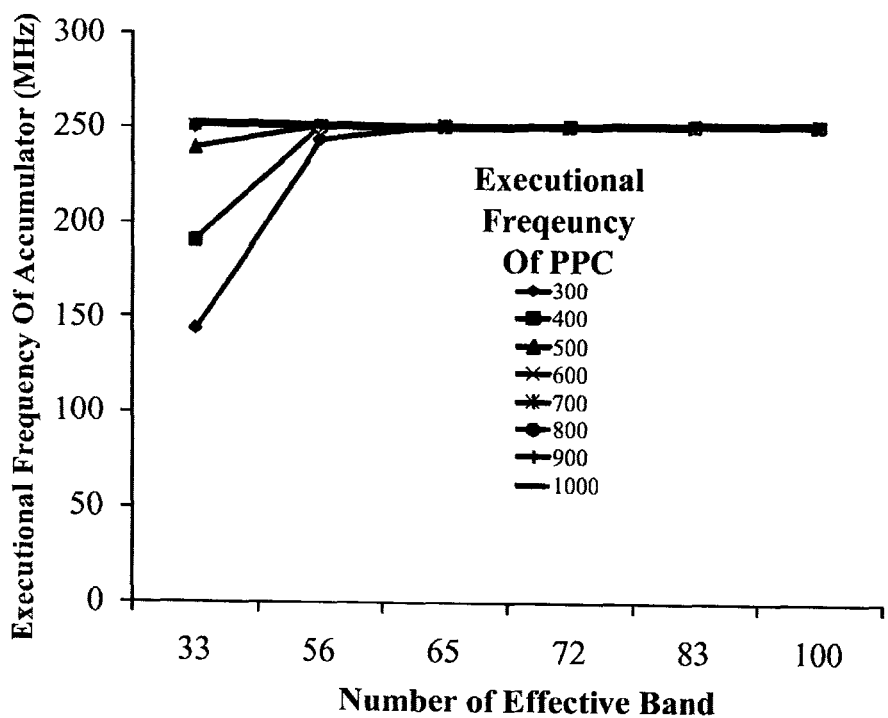

[FIG. 27]
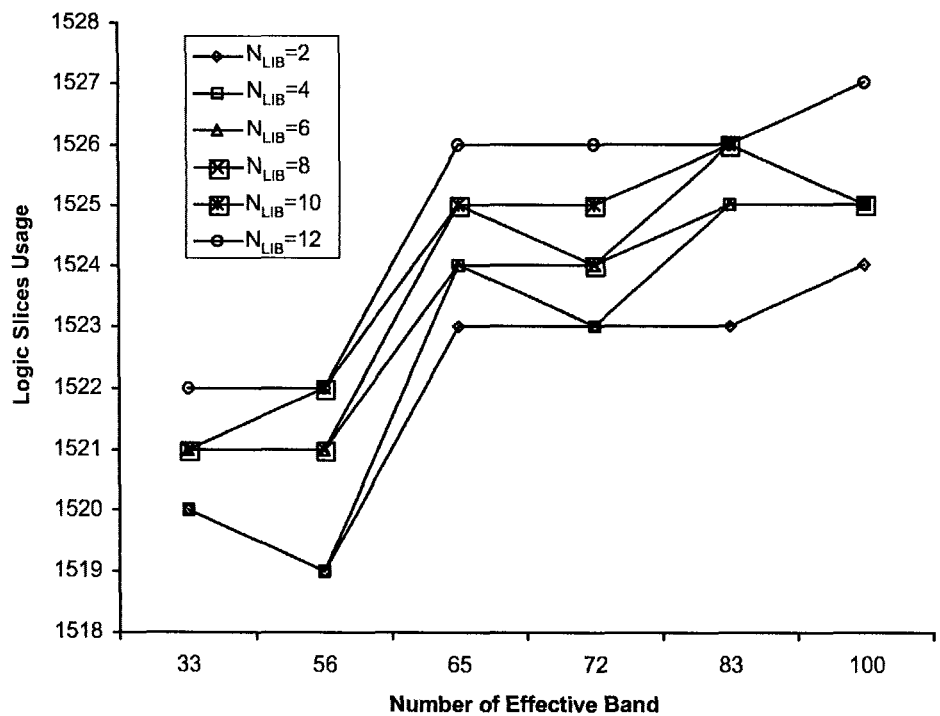
[FIG. 28]
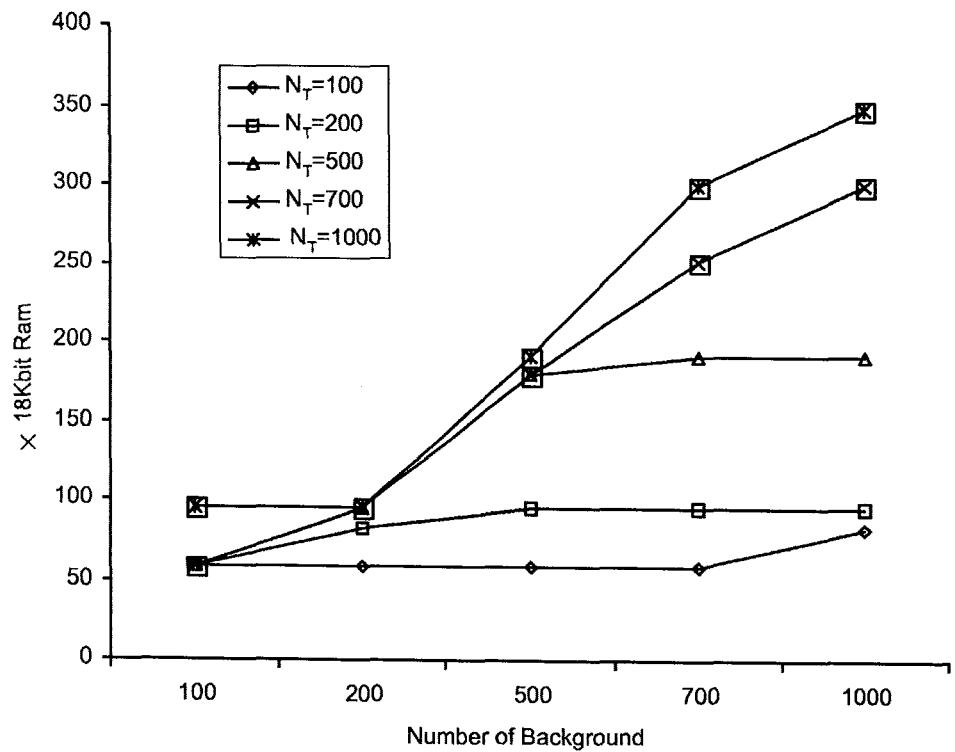

[FIG. 29]
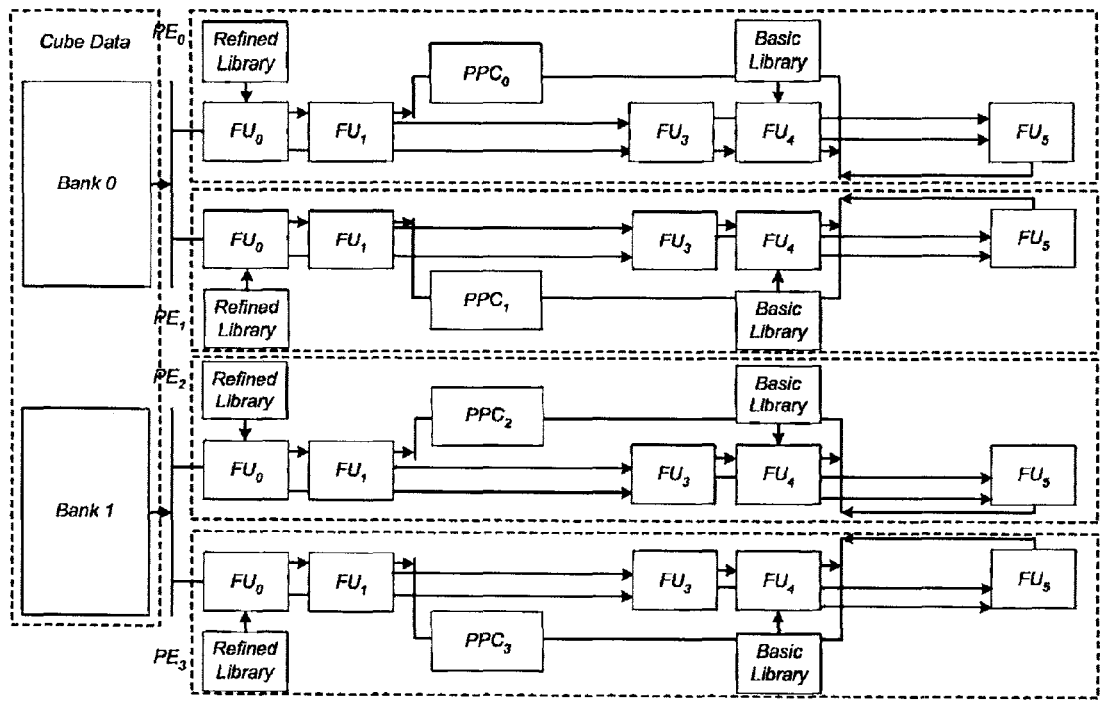
[FIG. 30]
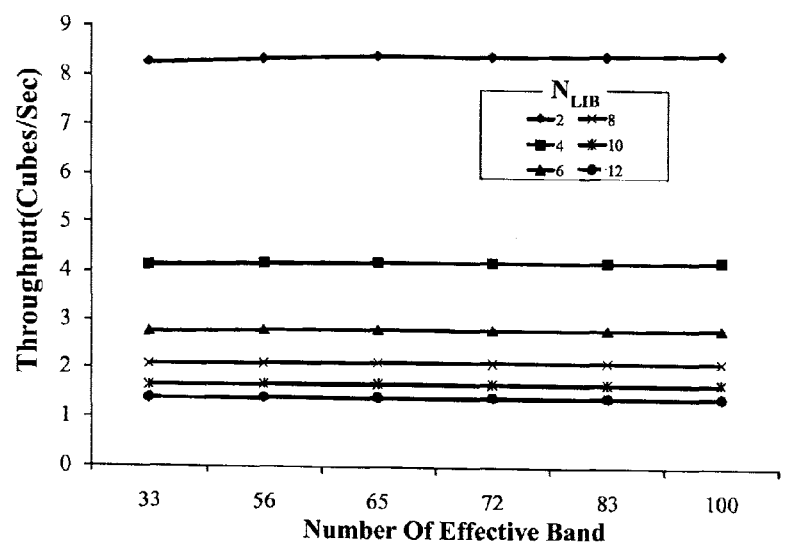

[FIG. 31]
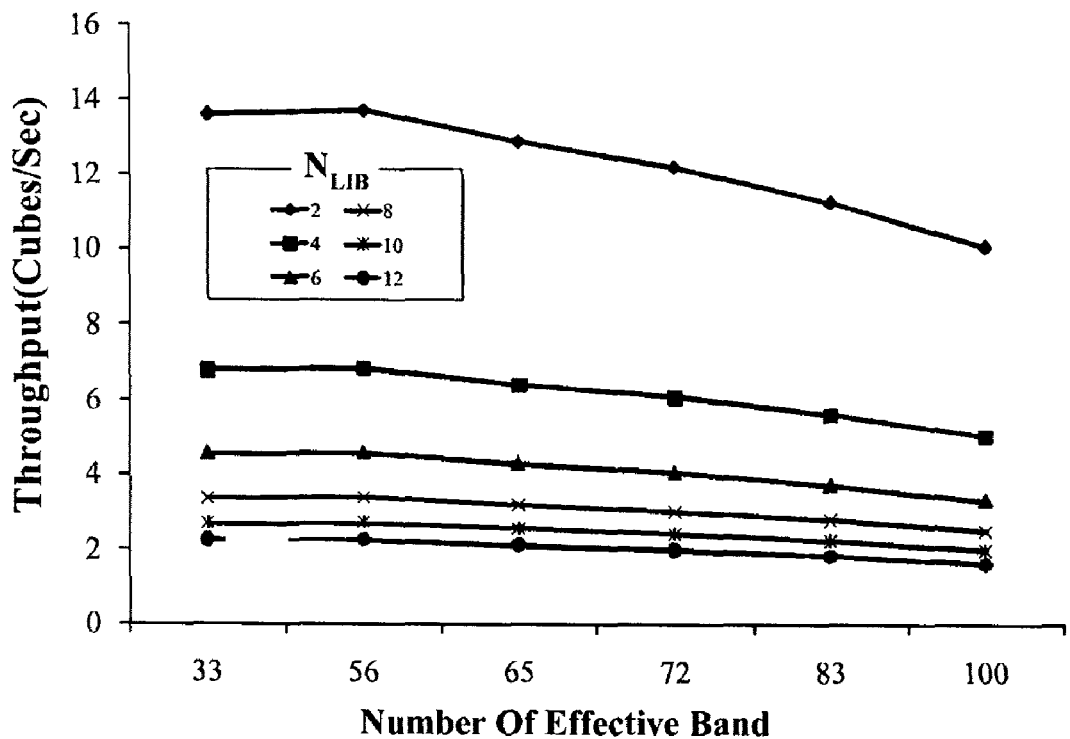
[FIG. 32]
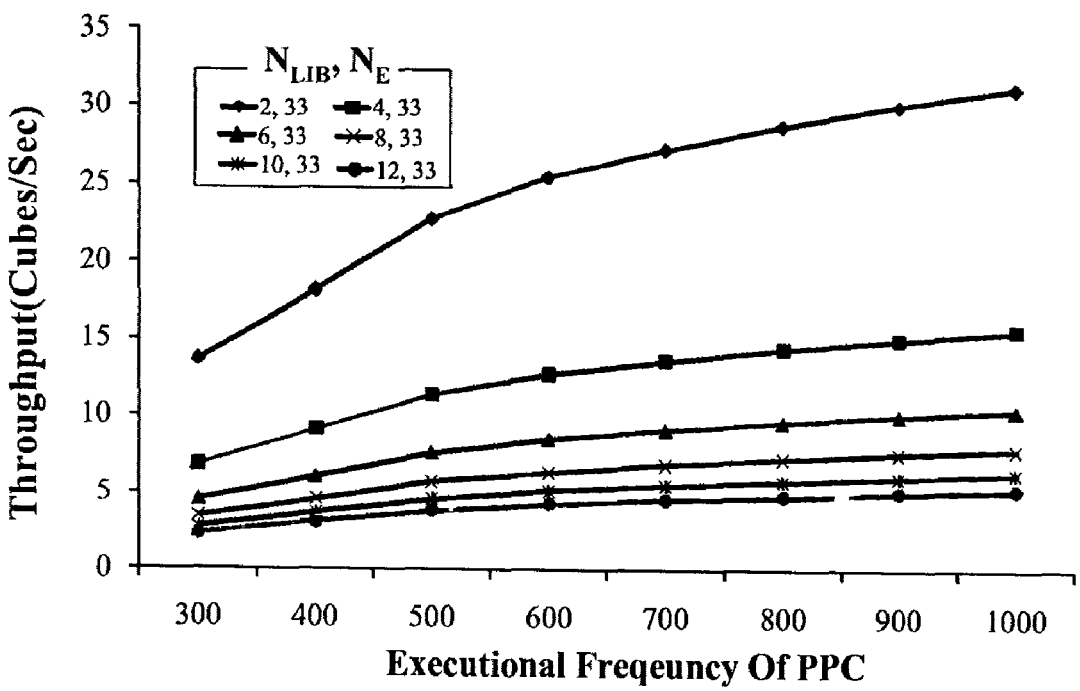

[FIG. 33]
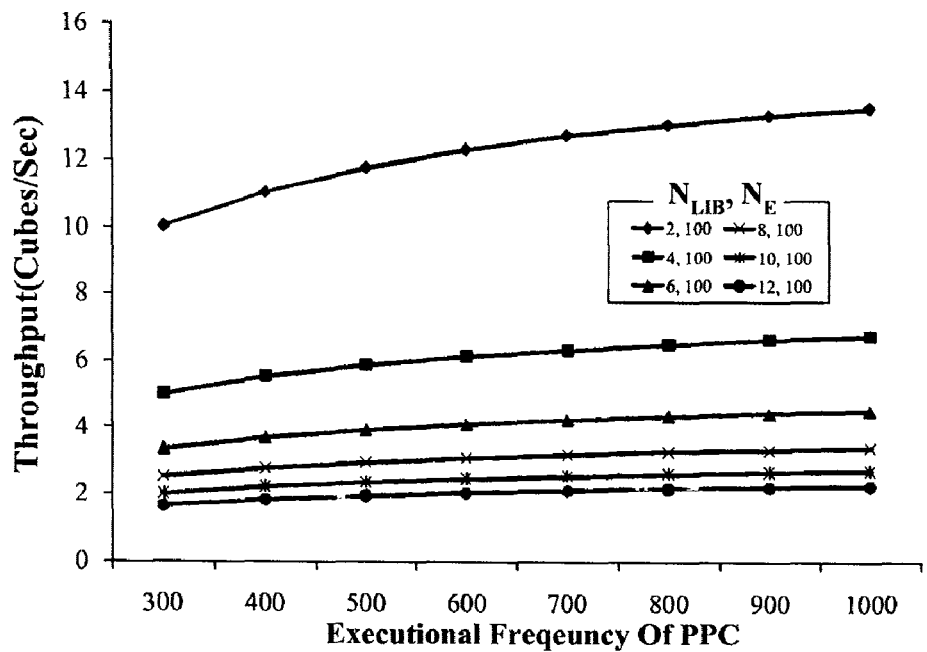
[FIG. 34]
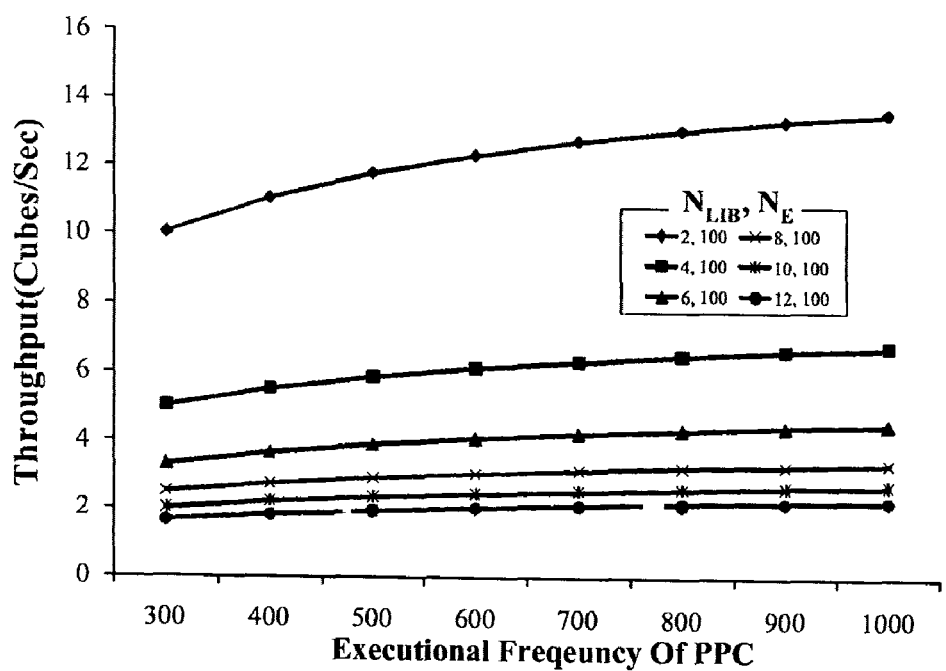

[FIG. 35]
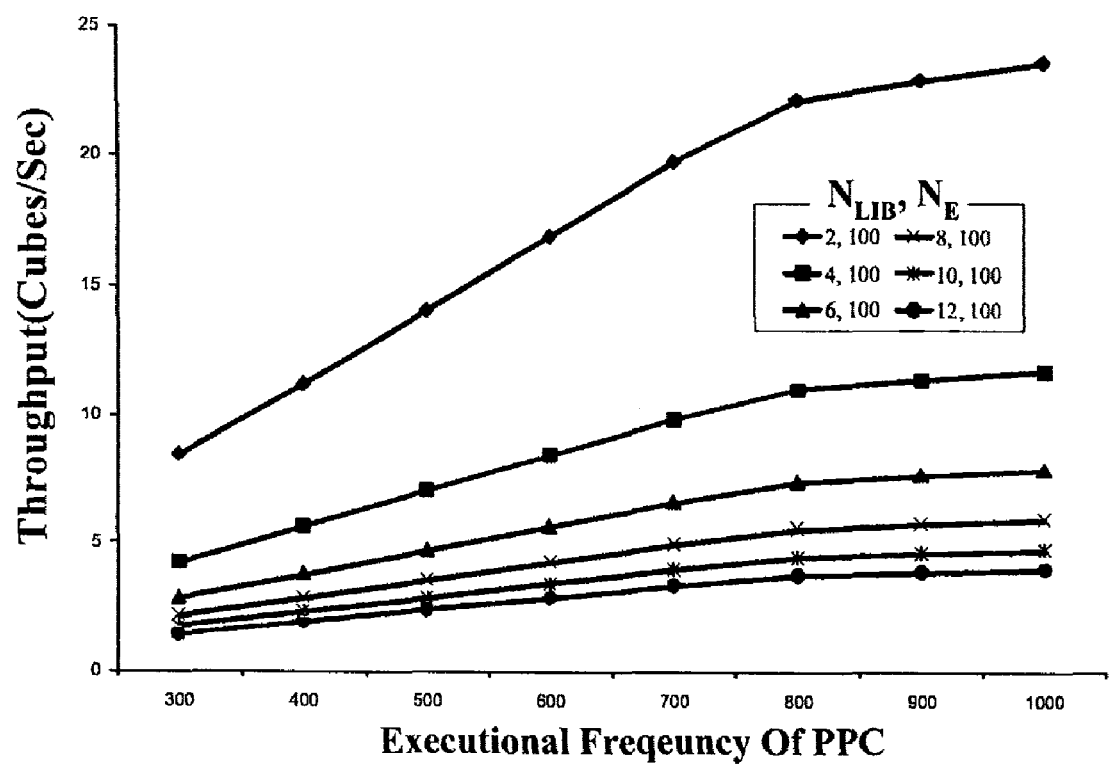

METHOD FOR REALTIME TARGET DETECTION BASED ON REDUCED COMPLEXITY HYPERSPECTRAL PROCESSING

CROSS-REFERENCE TO RELATED APPLICATIONS

This application is a national phase application of PCT Application No. PCT/KR2008/001840 filed on Apr. 2, 2008, which claims the benefit and priority to Korean Patent Application No. 10-2008-0017674 filed Feb. 27, 2008. The entire disclosures of the applications identified in this paragraph are incorporated herein by references.

TECHNICAL FIELD

The present invention relates to a real-time target detection method, and to more particularly, to a real-time target detection method for hyperspectral image processing.

BACKGROUND ART

The hyperspectral image processing is a technology which collects and interprets detailed spectral information from a scene. Image data for a pixel is represented in hundreds of narrow and adjacent spectral bands, virtually as a continuous spectrum. The spectral range includes infrared, visible and ultra-violet light. Detailed spectral resolution makes hyperspectral image technology a powerful tool for detecting chemical substances, anomalies and camouflaged objects, as well as for target-tracking. Traditional hyperspectral image processing uses hundreds of bands to detect or classify targets. The computational complexity is proportional to the amount of data needs to be processed. Thus, the data reduction and simplified algorithm are very critical for real-time execution. The computational complexity of the Hyperspectral processing can be reduced by exploiting spectral content redundancy so that partial number of bands can be used. However, the amount of data to be processed in the Hyperspectral image processing still large compared to that of typical image processing. There are many approaches for processing hyperspectral image data. Hardware clusters may be a feasible solution because these are used to achieve high performance, high availability or horizontal scaling. The cluster technology can also be used for highly scalable storage and/or data management. These computing resources could be utilized to efficiently process the remotely sensed data before transmission to the ground. Digital signal processors are also suitable for hyperspectral computations because it can be optimized for performing multiply-accumulate operations. It is usually implemented in DSP clusters for parallel processing. Traditional store-and-processing system performance is inadequate for real-time hyperspectral image processing without data reduction.

While conventional image pictures are represented by 2 dimensional matrices, the hyperspectral image has one more dimension for band spectral data as shown in FIG. 1. Collected data by hyperspectral image sensors are kept as one cube and each pixel which is located at (x; y) has Nz bands. Notations Nx and Ny are used for indicating total size of pixels in accordance to the axis. Implementing high performance for detection in hyperspectral images is a big challenge because of large number of spectral bands. The Hyperspectral image processing involves three key stages: Preprocessing, Processing, and Post-processing. The overall operation is illustrated in FIG. 2. A Hyperspectral sensor is an array of detectors where a detector collects a spectrum content in a pixel. The spectrum contents from sensors are stored in a cube memory structure as raw image data as shown in FIG. 2. The raw image data is calibrated by the Preprocessing. Each cube contains many numbers of bands which represents the characteristics of a target material. In the Processing, target images are detected by isolating the portion of data while it is highly correlated with the target library. The target library contains spectral information about the object that it is intended to detect. The objective of the Processing is to find out the target image from input cubes that correlates with spectral information stored in the target library. The third step is the Post-processing where actual detected images are displayed with RGB.

The main challenge of general hyperspectral image processing is the backside of its advantages: high volume and complexity of hyperspectral image data. For real-time processing, the complexity should be reduced. The easiest approach is to reduce the number of bands and the amount of library for processing. However, such reductions may eliminate the merit of the hyperspectral image processing. If certain bands have more characteristics to represent the object, all spectrums of bands do not need to detect the target. Thus, our approach determines which bands are more effective for the target detection and then use them to detect targets.

DETAILED DESCRIPTION OF THE INVENTION

Technical Problem

The present invention provides a real-time target detection architecture based on reduced complexity hyperspectral processing, the architecture capable of accurately detecting a target in a real-time quick application.

Technical Solution

According to an aspect of the present invention, there is provided a real-time target detection method based on hyperspectral processing, the method including: detecting a preprocessed pixel as a target and/or a background, based on a library; and refining the library by extracting target samples and background samples from the target and/or the background. Preferably, the refining the library may include making a list of effective bands for the pixel, based on contribution factor. Preferably, the detecting a preprocessed pixel as a target and/or a background may include: loading the list of effective bands from the refined library; obtaining spectrum information based on the list of effective bands and a correlation coefficient from the library; and determining the target and/or the background based on the size of the correlation coefficient. Preferably, in the determining the target and/or the background, when the correlation coefficient is greater than a least correlation coefficient indicating a relationship between the pixel and the library, the pixel may be detected as the target. Preferably, in the detecting a preprocessed pixel as a target and/or a background, the pixel may be processed using a pipeline structure.

Advantageous Effects

A real-time target detection architecture for hyperspectral image processing is based on a reduced complexity algorithm in which a library refinement procedure is simplified and the number of spectral bands is reduced for high throughput applications. An efficient pipeline processing element architecture using data partitioning is provided. A scalable multiple processing element architecture is provided. To improve speed, an interconnecting topology for the multiple processing element architecture is provided. There is provided a computing structure based on a data arrangement algorithm used in hyperspectral image processing to optimize processing unit modeling and memory using capabilities and eliminating a bottleneck status of memory. The proposed architecture is design and implemented in FPGA to verify the relationship between the hardware complexity versus the execution throughput of the reduced complexity hyperspectral image processing. Accordingly, the real-time target detection architecture for hyspectral image processing has a merit of quickly and accurately detecting a target.

BRIEF DESCRIPTION OF THE DRAWINGS

FIG. 1 is a diagram illustrating a cube data structure;

FIG. 2 is a block diagram illustrating overall hyperspectral image processing;

FIG. 3 is a diagram illustrating comparison of detected images where two different numbers of effective bands are applied;

FIG. 4 is a diagram illustrating a result of detected images when library refinement scheme is applied;

FIG. 5 is a flowchart illustrating a target detection method according to an embodiment of the present invention;

FIG. 6 is a timing chart illustrating processing where $N_{LIB}=4$;

FIG. 7 is a functional graph;

FIG. 8 is a diagram illustrating distribution of functions according to operations;

FIG. 9 is a diagram illustrating processing without cube delay;

FIG. 10 is a diagram illustrating processing where a pipeline structure with two stages is applied;

FIG. 11 is a timing chart illustrating the processing of FIG. 10;

FIG. 12 is a graph illustrating execution times with respect to TA and TB;

FIG. 13 is a diagram illustrating pixel-based pipeline structure at a stage A where three accumulators are applied;

FIG. 14 is a diagram illustrating execution times with respect to pixels in the pixel-based pipeline structure;

FIG. 15 illustrates the execution flow with the floating point units (FPUs);

FIG. 16 illustrates cube data partitioning where the number of processing elements is 4;

FIG. 17 illustrates cube partitioning;

FIG. 18 illustrates comparison of detected images where two different numbers of processing elements are applied;

FIG. 19 is a block diagram illustrating multiple data partitioning without separated library;

FIG. 20 is a block diagram illustrating multiple data partitioning with shared library;

FIG. 21 is a timing chart illustrating the multiple data partitioning of FIG. 20;

FIG. 22 is a block diagram illustrating processing according to an embodiment of the present invention;

FIG. 23 illustrates data transaction from bus to IP;

FIGS. 24 and 25 illustrate throughput respecting to the number of effective bands with one PPC and with two PPC, respectively;

FIG. 26 is a graph illustrating accumulator executional speed respecting to the number of effective bands with two PPCs;

FIG. 27 is a graph illustrating slice usage respecting to the number of the effective bands;

FIG. 28 is a graph illustrating block RAM size respecting to the number effective bands;

FIG. 29 illustrates an overall structure of the target detection in a multi processing execution model;

FIG. 30 illustrates throughput in four paths respecting to $N_{LIB}$ and $N_B$ with one PPC; and FIGS. 31 to 35 illustrate throughput in multiple paths respecting to $N_{LIB}$ and/or $N_E$ with two PPCs

BEST MODE FOR CARRYING OUT THE INVENTION

To fully understand advantages of operations of the present invention and the objects obtained by embodiments of the present invention, it is required to refer to attached drawings illustrating preferable embodiments of the present invention and contents shown in the drawings. Hereinafter, the preferable embodiments of the present invention will be described in detail with reference to the attached drawings. The same reference numerals shown in each drawing indicate the same elements.

The main operation in the hyperspectral image processing for target detection is to compare input cube image with the target library to determine the correlation coefficient in terms of spectrum contents. Hence, the main operation in hyperspectral image processing is the calculation of correlation. The correlation coefficient, A, is a measure of similarity between two spectrum contents which are stored in the target library and obtained from input images. High values of correlation between two spectrum contents indicate the high degree of similarity between the two. The correlation coefficient is defined as $$A = 1 - \cos^{-1}\left(\frac{\sum_{i=1}^{N_E} t_i r_i}{\sqrt{\sum_{i=1}^{N_E} t_i^2} \sqrt{\sum_{i=1}^{N_E} r_i^2}}\right) \quad (1)$$

where NE is the number of effective bands, ti is the test spectrum of ith band, and ri is the reference spectrum of ith band. We apply the effective band selection scheme to reduce the number of bands applied for the detection. For the scheme of effective band selection, we have defined a contribution factor which represents isolation effectiveness in terms of the target libraries. To obtain the contribution factor, we need randomly selected background samples which represent the spectral property of background images. Since the correlation represents the variation of differences between two spectrum contents, the effective bands are selected to get maximally separated contribution value.

FIG. 3 illustrates the comparison of detected images where two different numbers of bands (NE) are applied. In FIG. 3(a), we applied the effective band selection scheme where the flowers given targets are detected as well as FIG. 3(b). We improve the detection process by the library refinement which also reduces the complexity for execution time since the improved library can reduce the amount of library. In the application of the target detection, a library has a target spectrum which is generated in laboratories or measured in typical environments. Hence, the spectrum of target images measured by different conditions results in a mismatching of the target library. We refine the target library dynamically so that effective detection can be achieved with a small amount of the target library information. Thus, the scheme of library refinement improves the detection process. The overall process of library refinement starts with a set of basic library. Once a target image is detected from a library, the target library can be refined by the spectrum contents in a detected image. However, since the partial numbers of bands are used to get the sample in the effective band selection scheme, a target sample is a candidate for a new library. Thus, the new library applicant is compared to the basic library for entire bands and then used as a refined library.

FIG. 4 shows the results of library refinement where FIG. 4(b) and FIG. 4(c) use the refined library from the basic library in FIG. 4(a). These figures show that a given library can represent several types of different libraries. Hence, the library refinement can reduce the number of libraries applied.

FIG. 5 illustrates the overall algorithm for detecting and isolating target images. The algorithm has two processing flows. The right side is mainly related to the Detection which compares the input image with the library. The left side is for the Update for the library refinement and the effective band selection. Each operation is specified by Steps. Step 0, 1 and 2 exist for the Detection and others perform the Update. Step 0 loads the index of effective bands from Step 5 and then chooses spectrum contents of an input pixel and a library for effective bands. Step 1 has a loop to get the correlation coefficient (A) where the loop size is NLIBNE. Step 2a is for target detection and Step 2b is for background detection. In Step 2a, if the correlation coefficient (A) is over the minimum correlation coefficient between library and input image (At), the pixel is detected as a target and the spectrum contents in the pixel are reserved for the library refinement. Also, in order to choose background samples, the correlation coefficient (A) is compared to maximum correlation coefficient between input image and background (Ab) in Step 2b. Step 3 corrects samples for background and target. To represent the spectrum of background area, the samples of background are randomly selected. The library is refined in Step 4 and the effective bands are selected by using the contribution coefficient in Step 5.

There are several floating point operations such as root and arc-cosine functions in Step 1. Also, the detection function in Step 2 has floating point operations to compare the correlation coefficient (A) with At and Ab. However, the to output of Step 2 has integer data type. Also, the schemes of effective band selection and library refinement have floating point operations in Step 4 and Step 5. In [4], the most complex step for execution time is Step 1 which calculates the correlation coefficient (A). Step 3, 4, and 5 have less complexity than Step 1. Also the complexity is proportional to the number of effective bands and the number of libraries. However, the number of target and background samples does not have an effect on the overall complexity. The objectives of design are to assure fast operation of the Detection based on the correlation coefficient and to support the Update which contains the effective band selection and the library refinement. Two kinds of data dependencies exist in the processing flow.

At first, there is a cube delay. The results of the Update are the index of effective bands and refined libraries. However, these results can be applied from the next cube image. Second, the input image is duplicated to gather samples for the Update. The Detection uses the effective bands within input spectrum bands. However, the Update uses the detection result to obtain the target samples. Hence, the randomly selected target sample must be verified whether the target sample can replace the current library. To improve the execution time, we applied two approaches represented as the pipeline structure and the data partitioning. The pipeline is applied in single processing execution model. When the number of the Processing (NPE) is increased in multiple processing execution model, we expect the execution time for a cube (Tcube) is proportionally enhanced. However, there is the limitation from interconnection.

Hereinafter, there will be described basic concepts for the configuration of the architecture according to an embodiment of the present invention. First, there will be described a single processing execution model. Execution dependency will be described. To express the execution dependency of the hyperspectral image processing, a functional graph is showed as FIG. 7. Step 0 has two functions of load( ) and init( ) where the function load( ) corrects spectrum contents for effective bands from the Preprocessing and Refined Library and the function init( ) loads index of effective bands from the get eb( ) in Step 5. The function init( ) operates on each cube, but the function load( ) works on each pixel. Step 1 has the function acc( ) and the function corr( ) where the function acc( ) accumulates the inputs for effective bands. The accumulator has the operations of multiplication and summation as (1). The outputs of the function corr( ) are three fixed point numbers for $\Sigma ti^2$, $\Sigma ri^2$, and $\Sigma ti*ri$. Also, the function corr( ) calculates the correlation coefficient (A) which is a floating point number. The function detect( ) in Step 2 verifies the pixel from correlation coefficient (A) so that the operations of the function detect( ) are floating point operations. In Step 3, the function sample( ) corrects a sample for target or background in Step 0. Also, the function choose samples( ) chooses target and background samples. Step 4 has the functions loads( ), accs( ), corrs( ), dets( ), and saves( ) whose operations are similar to load( ), acc( ), corr( ), detect( ), and sample( ) but use all spectrum contents to refine the library. The functions diff( ), cont( ), and get eb( ) in Step 5 find the index of the effective bands based on the contribution factor so that the function has floating point operations as well as the fixed point operations.

FIG. 6 shows the overall execution timing flow. The execution time for a cube (Tcube) is denoted as Tinit+Tpixel-NxNy+Tcs+Trl+Tge where NxNy represents the spatial resolution of hyperspectral image cube, Tinit is the time of the function init( ) in Step 0, Tpixel is the execution time for a pixel, Tcs is the execution time of function choose samples( ) in Step 3, Trl is for the functions in Step 4, and Tge is the time of the functions in Step 5. When the spatial resolution is bigger, Tpixel is more significant. Tpixel is represented as (Tload+Tacc+Tcorr+Tdetect+Tsample)NLIB where Tload is the time of function load( ) in Step 0, Tacc is the time of function acc( ), Tcorr is the time of function corr( ) in Step 1, Tdetect is the time of function detect( ) in Step 2 and Tsample is the time of function sample( ). The functions in Processing have execution dependencies. The functions acc( ) and sample( ) use the same data from the Preprocessing but the operations of function samples( ) cannot be completed until the function detect( ) has results. Also, the functions in Step 4 load data from the function choose sample( ) but the function in Step 5 cannot start until the operations in Step 4 is done. Thus, the Detection is completed, the functions in Update can be processed.

A function expressed by a node in the graph can be separated as the pixel based function or the cube based function. The pixel based function operates per pixel but the cube based function works per cube. The functions load( ), acc( ), corr( ), detect( ), and sample( ) are the pixel based functions and the functions init( ), choose samples( ), loads( ), accs( ), corrs( ), dets( ), saves( ), diff( ), cont( ), and get eb( ) are the cube based functions. Note that the pixel based operation is more significant than the cube based operation in aspect of high speed execution since the pixel based operation executes NxNy times per cube but the cube based function executes only one per cube. The functions have two kinds of operations presented as fixed and floating point operations. FIG. 8 illustrates the functional partitioning where fixed point operations and floating point operations are separated by U0, U1, and U2. We denotes the floating point unit as U1, which contains the function corr( ) and detect( ) related to the Detection. Also, U2 contains the functions of dets( ), corrs( ), cont( ) and get eb( ) based on the floating to point operations.

There will be described the effects of pipeline architecture according to an embodiment of the present invention. In FIG. 8, the pixel based functions and the cube based functions are separated as Stage A and Stage B. Since the Update requires NTNLIB target samples and NB number of background samples, the result of the Update can be applied from next cube. Thus, the processing flow is based on two-stage pipeline which basically has cubes delay. The cube delay may decrease the speed of detection since the refined library and the effective bands index may not be available in the next cube image. However, in general, consecutive cube images have similar spectrum properties. Hence, if the cube delay time (TcubeNcube delay) is faster than the change of spectral properties (Tspectral), the cube delay can be allowed where Ncube delay is the number of cube delay. Note that Tspectral depends on the application of hyperspectral image processing. For example, once the hyperspectral image is used to detect a person in a surveillance system, the basic properties of light source is not changed suddenly so that the cube delay isn't significant.

In order to remove the cube delay, the Pre-detection step can be used in the Processing. FIG. 9 illustrates the block diagram of the Processing without the cube delay where all steps use the same cube image. Since the complex reduction schemes require background and target samples, the pre-detection composed by Step 1 and Step 2 is necessary to verify the randomly selected samples for full bands in Step 3. As we mentioned, NT number of target samples are required for the library refinement. Hence, to get NT number of target samples, the Pre-detection chooses and verifies bigger number samples than NT target samples. However, if the number of detected target pixels in the entire cube image is smaller than NT target samples, a cube image is necessary for the Pre-detection. In this case, the benefit of the effective band selection is disappeared.

There will be described a two-stage execution pipeline structure. FIG. 10 shows the block diagram of the Processing when the two stages pipeline structure is applied. The cube based execution pipeline, the Pipeline(1), separates the block diagram of the Processing to Stage A and Stage B.

In two-stages pipeline structure, the execution time for a cube (Tcube) is represented by:

$$T_{cube} = \max(T_A, T_B) \quad (2)$$

where TA and TB represent the execution time for Stage A and Stage B. TA is expressed as TpixelNxNy and TB is Tinit+Tcs+Trl+Tge. Once the number of bands is reduced, TA can be improved so that the overall execution time is reduced. However, the execution time of TB is not changed because the Update uses all spectrum contents. Hence, once the number of effective bands (NE) is smaller and/or the spatial resolution is lower, TB is more significant for overall execution time. FIG. 11 shows the time flow in the two-stages pipeline structure. The effective bands and refined library from ith cube can be applied from (i+2) th cube. Thus, the two-stages execution pipeline has two cubes delay.

In the single processing execution model, the execution time of Stage A (TA) is dominant for overall execution time. For example, in [4], TA is 18 times longer than TB. FIG. 12 shows the execution time of TA and TB where TA A TB. Thus, to enhance the execution time of hyperspectral image processing, smaller TA is necessary.

In order to improve the execution time of Stage A, we consider an internal pipeline structure presented by the pixel based execution pipeline. The pixel based execution pipeline does not have the cube delay but has the pixel delay between stages. Once the pixel based execution pipeline is applied, the execution time for a pixel (Tpixel) is critical for the execution time of Stage A (TA) where Tpixel is the maximum execution time between stages. For example, in FIG. 13, the pixel based execution pipeline structure is applied and three accumulators are used. In this figure, the minimum execution time for a pixel can be the same as the execution time for an accumulator (Tacc). The objective of the pixel based execution pipeline is to minimize the execution time for a pixel (Tpixel). FIG. 14 shows the execution time for a pixel (Tpixel) where the pixel based execution pipeline structure is fully applied. Thus, the limitation of the pixel based execution pipeline is represented as $$T_{pixel} = \left(\frac{3T_{acc}}{N_{acc}}\right)N_{LIB} = (T_{corr} + T_{detect})N_{LIB} \quad (3)$$

where 1·Nacc·3. If one accumulator is applied, the execution time for a pixel (Tpixel) is increased as three times.

The execution time for the floating point operations (Tcorr+Tdetect) can limit the execution time for a cube (Tcube) as well as the execution time of the accumulation (Tacc). Once the effective band selection algorithm is applied, the execution time of an accumulator (Tacc) can be reduced. Therefore, the execution time for the floating point operations (Tcorr+Tdetect) is significant in the reduced complexity hyperspectral image processing.

We consider the sharing of floating point units. In FIG. 8, U1 and U2 are to the floating point units.

FIG. 15 illustrates the execution flow with the floating point units (FPUs) where FIG. 15(a) uses one FPU and FIG. 15(b), (c) use two FPUs based on different time multiplexing. When one FPU is available, the execution time for a cube (Tcube) is the same as TA+TB where TA=TD1=TF1 and TB=TD2=TF2. The TD1 and TD1 are the execution times of the fixed point operations in Stage A and Stage B. Also, TF1 and TF2 are the execution time of floating point execution time in Stage A and Stage B. If two FPUs are available, each FPU can support Stage A or Stage B. Also, in FIG. 15(b), two FPUs work for Stage A at the same time and then a FPU can be applied to Stage B. Note that if one FPU is faster than the other, FIG. 15(b) can be a good example. Also, when the execution time for Stage A (TA) is much longer than the execution time for Stage B (TB), FIG. 15(c) can be a better choice. In 15(b), Tcube is the same as TA where TD1=TF1 and, in 15(c), Tcube is expressed as T' A=T' F1+TF2 where T' A=T' D1=T' F1=TF1=2.

There will be described the input capacity of the architecture according to an embodiment of the present invention.

The input capacity limits the overall execution time. We define the input capacity NbitFm, where Nbit represents the input bit-width and Fm denotes the maximum input frequency. To assure the execution of the Processing, the input capacity (NbitFm) is bigger than NxNyNzNreNTh where Nre represents the resolution of a spectrum content and NTh is the throughput which is the same as the number of cubes per second. In the above, the single processing execution model has been described. Hereinafter, there will be described a multiple processing execution model.

There will be described data partitioning. The objective of the data partitioning is to reduce the execution time by using the multiple processing elements (PEs). The type of data partitioning depends on the cube memory structure. FIG. 16 shows the three kinds of cube data partitioning which applies four numbers of PEs. FIGS. 16(a) and (b) separate the area of cube as 4 banks. Since each PE is connected to a bank memory, the limitation of input capacity with respect to the PE is the same as the single processing execution model. Also, in FIG. 16(c), each pixel is allocated to the different PE so that the cube image allocated in a PE is a low resolution cube image.

The execution time for a cube (Tcube) in the multiple processing execution model is represented as:

$$T_{cube} = \max(T_A/N_{PE}, T_B) \quad (4)$$

Thus, the data partitioning can improve the execution time. The increased number of PEs affects Stage A since the spatial image area of a PE is proportionally reduced to the NPE. Therefore, once NPE is increased, the overall execution time (Tcube) is finally limited as TB. Even if the cube is partitioned by several banks, the data type of each PE is still a cube as FIG. 17. The cube size in FIGS. 16(a) and (c) is $$\left(\frac{N_x}{2}\right)\left(\frac{N_y}{2}\right)N_z$$

and the cube size in FIG. 16(b) is $$\left(\frac{N_x}{4}\right)N_y N_z.$$

In FIGS. 16(a) and (b), each PE uses the different refined library and effective bands index so that the detected image can have boundaries between PEs. FIG. 18 shows the comparison of detected images where two different numbers of processing elements are applied. FIG. 18(a) uses one processing element is applied while FIG. 18(b) uses four processing elements. The detected image in FIG. 18(b) is similar to the result of one processing element in 18(a). The reason is that the detected image still satisfies the condition of detection (At≧0.9) even though the refined library is different. Hence, the multiple processing execution model based on the data partitioning can be a solution to enhance the execution time in the hyperspectral image processing. However, once lower At is used for the detection condition, the boundary between the detected images can be clearer since the refined library of a processing element can be more different than others in the lower At. Note that even if there is a boundary between the processing elements, the detected image is fair because the detected image satisfies the detection condition between the image and the refined library. However, the boundary can make misunderstanding since the Post-processing may use an edge detection scheme to combine the detected image and RGB image. Therefore, the Update sharing is necessary between the PEs. Note that in the case of FIG. 16(c) the Update sharing isn't necessary since each PE uses the similar low resolution image. There will be described Update Sharing. FIG. 19 shows the block diagram in the multiple data partitioning without the Update sharing where a PE is connected with the Preprocessing and the Post-processing through the interconnection networks. Stage A has three signals represented as Initial, Sample, and Refined library to send the index of effective bands and refined library and receive the samples for the Update. Thus, the Update is independent between processing elements.

In the multiple processing execution model, the interconnection network is a limitation of speed enhancement since the input capacity should follow the increased requirement. The input capacity is related to both the input frequency and the input bit-width (Nbit). However, since the input frequency is dedicated to the implemented architecture, the bit-width should be increased to support the speed up. The bigger input bit-width increases the complexity of interconnection so that the speed up from applying multiple processing elements is limited by the interconnection network. Once the Update sharing is necessary, Stage B is shared as FIG. 20 where Stage B contains the Update. To transfer the index of effective band and the refined library from Stage B to all processing element, all processing elements stop their execution and then execute Stage B per cube. Therefore, the execution time for a cube (Tcube) is represented as TA=NPE+TB in the case of Update sharing. TA can be improved by NPE but TB is not changed so that the execution time of Stage B limits the speed up as well as the limitation of interconnection network.

FIG. 21 illustrates the time flow in the multiple data partitioning with the shared Update.

Hereinafter, there will be described a detailed configuration of the architecture according to an embodiment of the present invention. First, there will be described a single processing element. A target platform will be described. Xilinx FPGA Virtex 4 FX 100 device is chosen to implement the architecture. The floating point operations can be implemented with Power PC Core (PPC) in FX FPGA. Typically PPC executes at the maximum speed of 400 (MHz). The chosen device has 6; 768£16 (bit) block ram that is enough size to support the memory requirement. FIG. 22 describes the overall processing in the single processing model. The FU0, FU1, FU3, FU4, and FU5 correspond to Step 0, Step 1, Step 3, Step 4, and Step 5, respectively. Also, PPC1 takes the operation of Step 2 and the floating operation in Step 1. Similarly, PPC2 takes the floating operations in Step 4 and Step 5.

There will be described functional units. Since the index of the effective band doesn't have a regular interval index, BUFSP is necessary to store the input spectral contents where the buffer has several banks and a bank has all spectral contents for a pixel. FU0 consists of three buffers. Once a spectrum content from Preprocessing is written in a bank, FU1 reads the effective spectrum contents from the other bank. Thus, the reading and writing operations rotate so that the read/write operations can process without any stoppage. Also, samples are corrected in BUFTG. Since a sample is stored until FU3 is ready to read, the size of BUFTG is proportional to the number of pixel based pipeline stages.

FU1 consists of three Accumulators. For an accumulated value with a pixel and a library, the Accumulator requires NE times read operations from BUFSP and BUFLIB. The accumulator is designed to execute a loop operation with a multiplier, an adder, and a multiplexer. PPC1 calculate the floating point operation for the correlation coefficient which has multiplication, root, and division operations. Also, the correlation coefficient is compared to the maximum correlation coefficient and minimum correlation coefficient to detect whether the pixel is a target or background. For storing background and target samples, FU3 has two buffers. Incoming spectral data sp come through one data path and are selected by writing enable signals. Incoming signal en tg indicates whether the pixel is a target. Likewise, once the signal en bk is '1', the pixel is stored into BUFbk as a background sample. The controller generates en tg signal and en bk.

FU4 is similar to FU1 but the operation requires all spectrum contents for a target sample from BUFtg. The contribution factors are extracted in FU5. Since the total execution time of two adders and 2's Complement unit is greater than incoming data time, a register is inserted after 2's Complement unit. Similarly the summation execution time of the abs( ) operator and the adder is over than the incoming data ratio so one register inserted after the abs( ) operator.

There will be described floating unit sharing. The PPC in target FPGA has three types bus architecture, processor local bus (PLB), device control register (DCR) and on the chip peripheral bus (OPB). PLB provides the fastest data transaction but it is designed for transferring program memory. Usually OPB and DCR connect with logic blocks. Even if their performance is similar, DCR does not provide functional simulation. Since data transaction can be checked by functional simulation. In our design, the OPB is selected for floating unit sharing. The allowed and supported integer clock frequency ratios between the processing element and the OPB are 1:1, 2:1, 3:1 up to 16:1. FIG. 23 illustrates how functional blocks send data to the PPC. First BUS2IP WrCE signal notifies the beginning transaction. If the functional block is not ready to send a signal, the functional blocks reply IP2BUS Retry signal and OPB repeats the same transaction until receiving the acknowledgement signal. FIG. 23 shows both operations and the first transaction as an example of not ready status. The functional units are mapped by the address and predefined addresses are used to distinguishing the logic blocks.

There will be described discussion on overhead and throughput. FIGS. 24 and 25 show the difference between using one and two PPCs. As shown in the two figures, 2.1099 cubes are detected per second when one PPC is used but 3.2196 cubes possible by using two PPCs. The executional speed of the accumulator in FU1 should be less than 64 (MHz) even though it can execute 250 (MHz) in maximum speed. The number of effective bands is important factor in determining the executional speed of an accumulator as shown in FIG. 26. This figure is drawn when the PPC is operated in different executional frequencies. To support fast operation of accumulators, the faster PPC is necessary. Note that using one processor for both operations Detection and Update becomes serious bottle-neck in aspect of overall throughput.

FIG. 27 shows slice usage respecting to the number of the effective band. Different curves correspond to different numbers of libraries. There are four factors for determining the complexity of the overall design, such as NE, NLIB, NT and NB.

NT and NB are important factors in determining the memory size. FIG. 28 shows the number of the used 18 (KBit) block ram according to NB. As shown in FIG. 28, maximum supportable memory size is limited at 1000*1000 because the chosen device has 376*18 (KBit) block rams. Comparing to the maximum number of logic slices 42,176, NT and NB become dominant factors in the aspect of complexity. Thus, NE and NLIB, affect the overall throughput and NT and NB are critical for memory complexity.

In the above, there has been described the architecture structure in the single processing execution model. Hereinafter, there will be described a multiple processing execution model. First, there will be described interconnect type and multiple PE. To enhance performance, the multiple processing execution model is introduced. FIG. 29 shows that the input data stream comes through bus. The target FPGA must support the pin assignment as the direct connection band width. For example, 152 I/O pads are required for (address)=100, (data)=48 and others for controllers such as writing enable signals when the picture has 640*512*224 size with 4 processing elements. Our target FPGA supports 768 I/O pads. Each processing element and bank has the same speed because processing elements access its one classified bank.

Two processing elements share the bus and incoming data are multiplexed (i.e processing element 1 and 2 accesses only bank 1 in the external memory). Since single port block performs as 355 (MHz) in maximum speed, implementing with one bus architecture is impossible when each single processing element executes at 125 (MHz).

The bus connection is selected to implement because floating operators in PPC executes sequentially a logic blocks which are parallel. Overall throughput is determined by skewed path operation of the PPC. Incoming data does not need to parallel and direct connection consumes 2 times I/O pads at least. Most of all, bus type saves buffer size because writing operation becomes same with reading operation. Even though the writing data time is fast, it does not affect the overall throughput because bottle neck speed comes from the executional time of accumulator.

While each processor core is dedicated for the Detection and Update in single path, one core operates both in multiple paths as shown in FIG. 29. Throughput will be analyzed. FIG. 30 illustrates detected hyperspectral image numbers in according to NB when the detection is processed with 4 processing elements. Different curves denote different NLIB and each processing element is implemented by one PPC. As shown in the figure, overall throughput does not change even though the number of background samples is increased. Throughput is increased only when NLIB is decreased. This graphs shows that NB does not affect the overall throughput because the executional speed of the PPC becomes the bottleneck of throughput.

FIG. 31 shows the same condition as FIG. 34 except the number of implemented PPCs. FIG. 31 is considered a case of two PPCs in each processing element. The throughput is highly related to NE and NLIB. This relationship can be analyzed by FIGS. 32 and 33. Both graphs show estimated throughput with four processing elements and each processing has two PPCs. A real-time target detection architecture for hyperspectral image processing is proposed in this paper. The architecture is based on a reduced complexity algorithm for high throughput applications. Multi-level pipelining of the architecture enhanced the overall throughput and the architecture is scalable so that the execution speed improves with the number of processing elements. The proposed pipelining also minimized overall memory usage and effect of memory speed bottleneck. The proposed architecture is design and implemented in FPGA to verify the relationship between the hardware complexity versus the execution throughput of the reduced complexity hyperspectral image processing.

INDUSTRIAL APPLICABILITY

The real-time target detection method according to an embodiment of the present invention may be applied to the field of ubiquitous industry, and more particularly, to the field of computer architecture.

The invention claimed is:
1. A method for real-time target detection, based on hyperspectral processing, the method comprising:
    detecting a preprocessed pixel as a target and/or a background, based on a library; and refining the library by extracting a target and/or background sample from the target and/or the background.

2. The method of claim 1, wherein the refining the library comprises making a list of effective bands for the pixel based on a contribution factor.

3. The method of claim 1, wherein the detecting a preprocessed pixel as a target and/or a background comprises:

loading the list of effective bands from a refined library;

obtaining spectrum information based on the list of effective bands and a correlation coefficient from the library; and determining the target and/or the background based on the size of the correlation coefficient.

4. The method of claim 3, wherein, in the determining the target and/or the background, when the correlation coefficient is greater than a least correlation coefficient indicating a relationship between the pixel and the library, the pixel is detected as the target.

5. The method of claim 1, wherein, in the detecting a preprocessed pixel as a target and/or a background, the pixel is processed using a pipeline structure.

* * * * *